(12) United States Patent
Wisbey et al.

(10) Patent No.: US 10,078,734 B2
(45) Date of Patent: Sep. 18, 2018

(54) SYSTEM AND METHOD FOR IDENTIFYING PERFORMANCE DAYS USING EARPHONES WITH BIOMETRIC SENSORS

(71) Applicant: LOGITECH EUROPE, S.A.

(72) Inventors: Ben Wisbey, Canberra (AU); David Shepherd, Canberra (AU); Stephen Duddy, Moama (AU)

(73) Assignee: LOGITECH EUROPE, S.A., Lausanne (CH)

( * ) Notice: Subject to any disclaimer, the term of this patent is extended or adjusted under 35 U.S.C. 154(b) by 267 days.

(21) Appl. No.: 14/871,822

(22) Filed: Sep. 30, 2015

(65) Prior Publication Data

US 2016/0026856 A1 Jan. 28, 2016

Related U.S. Application Data

(63) Continuation-in-part of application No. 14/830,549, filed on Aug. 19, 2015, and a continuation-in-part of application No. 14/140,411, filed on Dec. 24, 2013, which is a continuation-in-part of application No. 14/137,734, filed on Dec. 20, 2013, now abandoned,
(Continued)

(51) Int. Cl.
| | |
|---|---|
| *G16H 20/30* | (2018.01) |
| *A61B 5/00* | (2006.01) |
| *A61B 5/024* | (2006.01) |
| *G08B 21/04* | (2006.01) |
| *G06F 19/00* | (2018.01) |

(52) U.S. Cl.
CPC ...... *G06F 19/3481* (2013.01); *A61B 5/02416* (2013.01); *A61B 5/6815* (2013.01); *G16H 20/30* (2018.01); *G08B 21/0446* (2013.01)

(58) Field of Classification Search
CPC ............ G06F 19/3481; A61B 5/02416; A61B 5/6815; G08B 21/0446; G16H 20/30
See application file for complete search history.

(56) References Cited

U.S. PATENT DOCUMENTS

| | | |
|---|---|---|
| 2,189,096 A | 2/1940 | Alonge |
| 3,543,724 A | 12/1970 | Kirkpatrick et al. |
| (Continued) | | |

OTHER PUBLICATIONS

"Elite Clock Military Style LED Watch" by ledwatchsuk. YouTube [dated May 31, 2011][online][retrieved on Aug. 14, 2015].
(Continued)

*Primary Examiner* — William H McCulloch, Jr.
(74) *Attorney, Agent, or Firm* — Patterson & Sheridan, LLP

(57) ABSTRACT

Systems and methods are provided for using earphones with biometric sensors to identify and present information regarding performance periods. Fatigue level associated with fatigue experienced in response to a stimulus and recovery from such fatigue may be determined based on heart rate variability (HRV) data and learned user characteristics. One or more cycles of fatigue and recovery can be identified as a fitness cycle(s), each fitness cycle encompassing a period of time beginning with the stimulus associated with the fitness-related activity and progressing through recovery from the fatigue experienced in response to the stimulus associated with the fitness-related activity. A performance period may be predicted based on a pre-determined fatigue/recovery level instance within a fitness cycle.

20 Claims, 23 Drawing Sheets

Related U.S. Application Data which is a continuation-in-part of application No. 14/062,815, filed on Oct. 24, 2013, now abandoned.

(56) References Cited

U.S. PATENT DOCUMENTS

| | | | |
|---|---|---|---|
| 3,978,849 | A | 9/1976 | Geneen |
| 4,129,124 | A | 12/1978 | Thalmann |
| 4,224,984 | A | 9/1980 | Cramer et al. |
| 4,307,727 | A | 12/1981 | Haynes |
| 4,331,154 | A | 5/1982 | Broadwater et al. |
| 4,407,295 | A | 10/1983 | Steuer et al. |
| 4,409,983 | A | 10/1983 | Albert |
| 4,491,970 | A | 1/1985 | Lawhite et al. |
| 5,301,154 | A | 4/1994 | Suga |
| 5,392,261 | A | 2/1995 | Hsu |
| 5,406,952 | A | 4/1995 | Barnes et al. |
| 5,524,637 | A | 6/1996 | Erickson |
| 5,734,625 | A | 3/1998 | Kondo |
| 5,755,623 | A | 5/1998 | Mizenko |
| 5,899,370 | A | 5/1999 | Bould |
| 6,151,968 | A | 11/2000 | Chou |
| 6,361,503 | B1 | 3/2002 | Starobin et al. |
| 6,736,759 | B1 | 5/2004 | Stubbs et al. |
| 7,192,401 | B2 | 3/2007 | Saalasti et al. |
| 7,717,827 | B2 | 5/2010 | Kurunmaki et al. |
| 7,914,425 | B2 | 3/2011 | Hanoun |
| 8,788,002 | B2 * | 7/2014 | LeBoeuf ............... A61B 5/0077 600/310 |
| 8,888,701 | B2 * | 11/2014 | LeBoeuf ................ G16H 40/63 600/301 |
| 8,929,965 | B2 * | 1/2015 | LeBoeuf ............... A61B 5/0077 600/310 |
| 8,942,776 | B2 * | 1/2015 | LeBoeuf ............... A61B 5/0077 600/310 |
| 8,992,385 | B2 | 3/2015 | Lemos |
| 9,314,167 | B2 * | 4/2016 | LeBoeuf ............... A61B 5/0205 |
| 9,538,921 | B2 * | 1/2017 | LeBoeuf |
| 9,622,685 | B2 * | 4/2017 | Wisbey ................ A61B 5/0205 |
| 9,788,794 | B2 * | 10/2017 | LeBoeuf ................ G16H 40/63 |
| 2002/0151811 | A1 | 10/2002 | Starobin et al. |
| 2002/0188210 | A1 | 12/2002 | Aizawa |
| 2003/0065269 | A1 | 4/2003 | Vetter et al. |
| 2005/0056655 | A1 | 3/2005 | Gary |
| 2005/0116811 | A1 | 6/2005 | Eros et al. |
| 2005/0256416 | A1 | 11/2005 | Chen |
| 2006/0079800 | A1 * | 4/2006 | Martikka ............ A61B 5/0488 600/546 |
| 2006/0183980 | A1 | 8/2006 | Yang |
| 2007/0118043 | A1 | 5/2007 | Oliver et al. |
| 2008/0076972 | A1 * | 3/2008 | Dorogusker ....... A61B 5/02055 600/300 |
| 2008/0086318 | A1 * | 4/2008 | Gilley .................... G06Q 10/06 705/319 |
| 2008/0132383 | A1 | 6/2008 | Einav et al. |
| 2008/0228089 | A1 | 9/2008 | Cho et al. |
| 2009/0281435 | A1 * | 11/2009 | Ahmed ............. A61B 5/02416 600/502 |
| 2009/0312656 | A1 | 12/2009 | Lau et al. |
| 2010/0016741 | A1 * | 1/2010 | Mix ................. A61B 5/02416 600/508 |
| 2010/0197463 | A1 | 8/2010 | Haughay, Jr. et al. |
| 2010/0217102 | A1 * | 8/2010 | LeBoeuf .................. A61B 5/00 600/310 |
| 2011/0021319 | A1 | 1/2011 | Nissila et al. |
| 2011/0092790 | A1 | 4/2011 | Wilder-Smith et al. |
| 2011/0260870 | A1 | 10/2011 | Bailey |
| 2012/0022341 | A1 | 1/2012 | Zdeblick |
| 2012/0168471 | A1 | 7/2012 | Wilson |
| 2012/0253485 | A1 | 10/2012 | Weast et al. |
| 2013/0064049 | A1 | 3/2013 | Pileri et al. |
| 2013/0131519 | A1 * | 5/2013 | LeBoeuf .............. A61B 5/0077 600/476 |
| 2013/0237778 | A1 | 9/2013 | Rouquette |
| 2013/0335226 | A1 * | 12/2013 | Shen ...................... H04R 5/033 340/573.1 |
| 2013/0336495 | A1 * | 12/2013 | Burgett ................ H04R 1/1091 381/74 |
| 2014/0032234 | A1 | 1/2014 | Anderson |
| 2014/0073486 | A1 | 3/2014 | Ahmed et al. |
| 2014/0107493 | A1 | 4/2014 | Yuen et al. |
| 2014/0219467 | A1 * | 8/2014 | Kurtz ...................... H04R 3/12 381/74 |
| 2014/0228175 | A1 | 8/2014 | Lemos et al. |
| 2016/0022200 | A1 * | 1/2016 | Wisbey .............. A61B 5/02438 434/236 |
| 2016/0023047 | A1 * | 1/2016 | Wisbey .............. G09B 19/0038 434/247 |
| 2016/0026856 | A1 * | 1/2016 | Wisbey ............... G06F 19/3481 700/91 |
| 2016/0027324 | A1 * | 1/2016 | Wisbey .................. G09B 19/00 434/247 |
| 2016/0029125 | A1 * | 1/2016 | Armstrong ............ A61B 5/1118 381/74 |
| 2016/0029974 | A1 * | 2/2016 | Armstrong ........... A61B 5/7278 600/301 |
| 2016/0051184 | A1 * | 2/2016 | Wisbey ................ A61B 5/0205 600/301 |
| 2016/0051185 | A1 * | 2/2016 | Wisbey .............. A61B 5/02438 705/2 |
| 2016/0361020 | A1 * | 12/2016 | LeBoeuf ................ G16H 40/63 |
| 2017/0049335 | A1 * | 2/2017 | Duddy ................ A61B 5/0205 |
| 2017/0127957 | A1 * | 5/2017 | Wisbey .............. A61B 5/02405 |
| 2017/0215742 | A1 * | 8/2017 | Wisbey ................ A61B 5/0205 |
| 2017/0216671 | A1 * | 8/2017 | Wisbey ............. A63B 24/0075 |
| 2017/0216672 | A1 * | 8/2017 | Wisbey ............. A63B 24/0075 |
| 2017/0216673 | A1 * | 8/2017 | Armstrong ........ A63B 24/0075 |
| 2017/0367658 | A1 * | 12/2017 | LeBoeuf ................ G16H 40/63 |

OTHER PUBLICATIONS

"watch Stylish Blue Light LED Round Dial Matrix Stainless from ChinaBuye.com" by YnopoB. YouTube [dated Apr. 23, 2012][online][retrieved on Dec. 31, 2015] (https://www.youtube.com/watch?v=e_LWbXHvvWg).

* cited by examiner

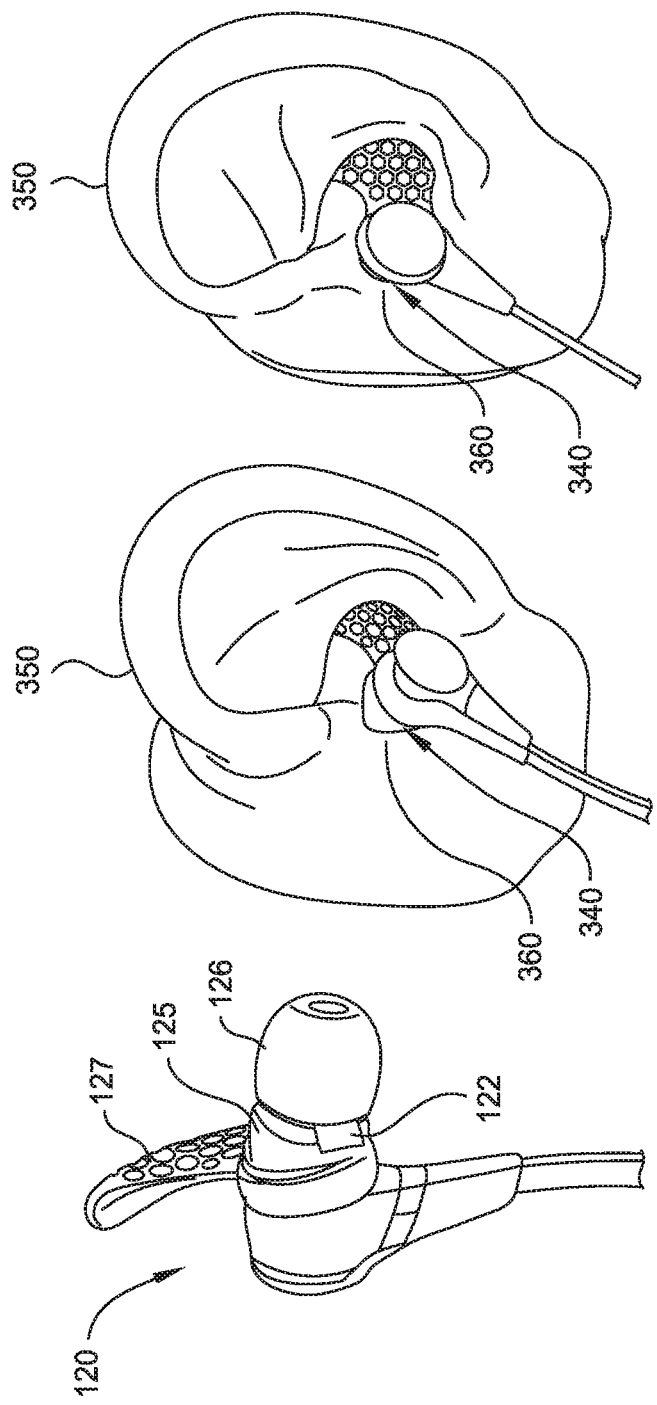

SYSTEM AND METHOD FOR IDENTIFYING PERFORMANCE DAYS USING EARPHONES WITH BIOMETRIC SENSORS

CROSS-REFERENCE TO RELATED APPLICATIONS

This application is a continuation-in-part of and claims the benefit of U.S. patent application Ser. No. 14/830,549 filed Aug. 19, 2015, titled "Earphones with Biometric Sensors," the contents of which are incorporated herein by reference in their entirety. This application is also a continuation-in-part of and claims the benefit of U.S. patent application Ser. No. 14/140,411 filed Dec. 24, 2013, titled "System and Method for Identifying Performance Days," which is a continuation-in-part of and claims the benefit of U.S. patent application Ser. No. 14/137,734, filed Dec. 20, 2013, titled "System and Method for Providing a Smart Activity Score," which is a continuation-in-part of U.S. patent application Ser. No. 14/062,815, filed Oct. 24, 2013, titled "Wristband with Removable Activity Monitoring Device," the contents all of which are incorporated herein by reference in their entirety.

TECHNICAL FIELD

The present disclosure relates to earphones with biometric sensors, and more particularly embodiments describe a systems and methods for identifying performance days using earphones with biometric sensors.

DESCRIPTION OF THE RELATED ART

Previous generation movement monitoring and fitness tracking devices generally enabled only a tracking of activity that accounts for total calories burned based on universal metabolic equivalent tasks. Currently available fitness tracking devices now add functionality that customizes metabolic equivalent tasks according to user characteristics. One issue with currently available fitness tracking devices is that they do not account for the performance or recovery state of the user in a scientific, user-specific way. Another issue is that currently available solutions do not account in a precise manner for the optimal relationship between activity and recovery.

BRIEF SUMMARY OF THE DISCLOSURE

In view of the above drawbacks, there exists a long-felt need for fitness monitoring devices that detect a fatigue level in a scientific way and provide user-specific recovery feedback based on actual, historical data. Furthermore, there is a need for fitness monitoring devices that provide increased resolution into the optimal balance between recovery and activity such that users can identify such periods (e.g., days) when they may achieve optimal performance when engaging in one or more activities.

Embodiments of the present disclosure include systems and methods for identifying periods when a user may achieve optimal performance when engaging in one or more activities.

In one embodiment, a system for identifying a performance period includes: a pair of earphones including: speakers; a processor; and a heartrate sensor electrically coupled to the processor, where the processor is configured to process electronic input signals from the heartrate sensor. The system also includes a memory coupled to a processor and having instructions thereon that, when executed by the processor, causes the system to: identify the user's progression through a plurality of fitness cycles, each of the plurality of fitness cycles encompassing a period from the beginning of a stimulus through recovery from the stimulus; and predict optimal performance periods based on the plurality of fitness cycles. In this embodiment, identifying the user's progression through a plurality of fitness cycles is based in part on signals generated by the heartrate sensor.

In one embodiment, the heartrate sensor is an optical heartrate sensor protruding from a side of the earphone proximal to an interior side of a user's ear when the earphone is worn. In this embodiment, the optical heartrate sensor is configured to measure the user's blood flow and to output an electrical signal representative of this measurement to the earphones processor.

In another embodiment, the earphones include a motion sensor, and the earphones processor is configured to process electronic input signals from the motion sensor. In implementations of this embodiment, the memory includes additional instructions that, when executed by a processor, causes the system to monitor a movement of the user based on signals generated by the motion sensor to determine if the movement is indicative of the stimulus.

In another embodiment, a system for identifying a performance period includes: a pair of earphones including: speakers; a processor; and a heartrate sensor electrically coupled to the processor, where the processor is configured to process electronic input signals from the heartrate sensor. The system also includes a memory coupled to a processor and having instructions thereon that, when executed by the processor, causes the system to: determine a fatigue level associated with fatigue experienced in response to a stimulus, where the fatigue level is determined based in part on signals generated by the heartrate sensor; determine a recovery level based at least in part, on the fatigue level; identify a fitness cycle, the fitness cycle comprising a segment of time beginning from the stimulus and progressing through recovery from the fatigue experienced in response to the stimulus; and predict an optimal performance period based on the identification of the fitness cycle.

Other features and aspects of the disclosed method and system will become apparent from the following detailed description, taken in conjunction with the accompanying drawings, which illustrate, by way of example, the features in accordance with embodiments of the disclosure. The summary is not intended to limit the scope of the claimed disclosure, which is defined solely by the claims attached hereto.

BRIEF DESCRIPTION OF THE DRAWINGS

The present disclosure, in accordance with one or more various embodiments, is described in detail with reference to the following Figures. The Figures are provided for purposes of illustration only and merely depict typical or example embodiments of the disclosure.

FIG. 3A illustrates a perspective view of a particular embodiment of an earphone, including an optical heartrate sensor, in accordance with the disclosed technology.

FIG. 3B illustrates a side perspective view of placement of the optical heartrate sensor of the earphones of FIG. 3A when they are worn by a user.

FIG. 3C illustrates a frontal perspective view of placement of the optical heartrate sensor of the earphones of FIG. 3A when they are worn by a user.

DETAILED DESCRIPTION

The present disclosure is directed toward systems and methods for identifying performance periods. In particular embodiments, the systems and methods are directed to earphones with biometric sensors that are used to identify performance periods.

Figure 1:
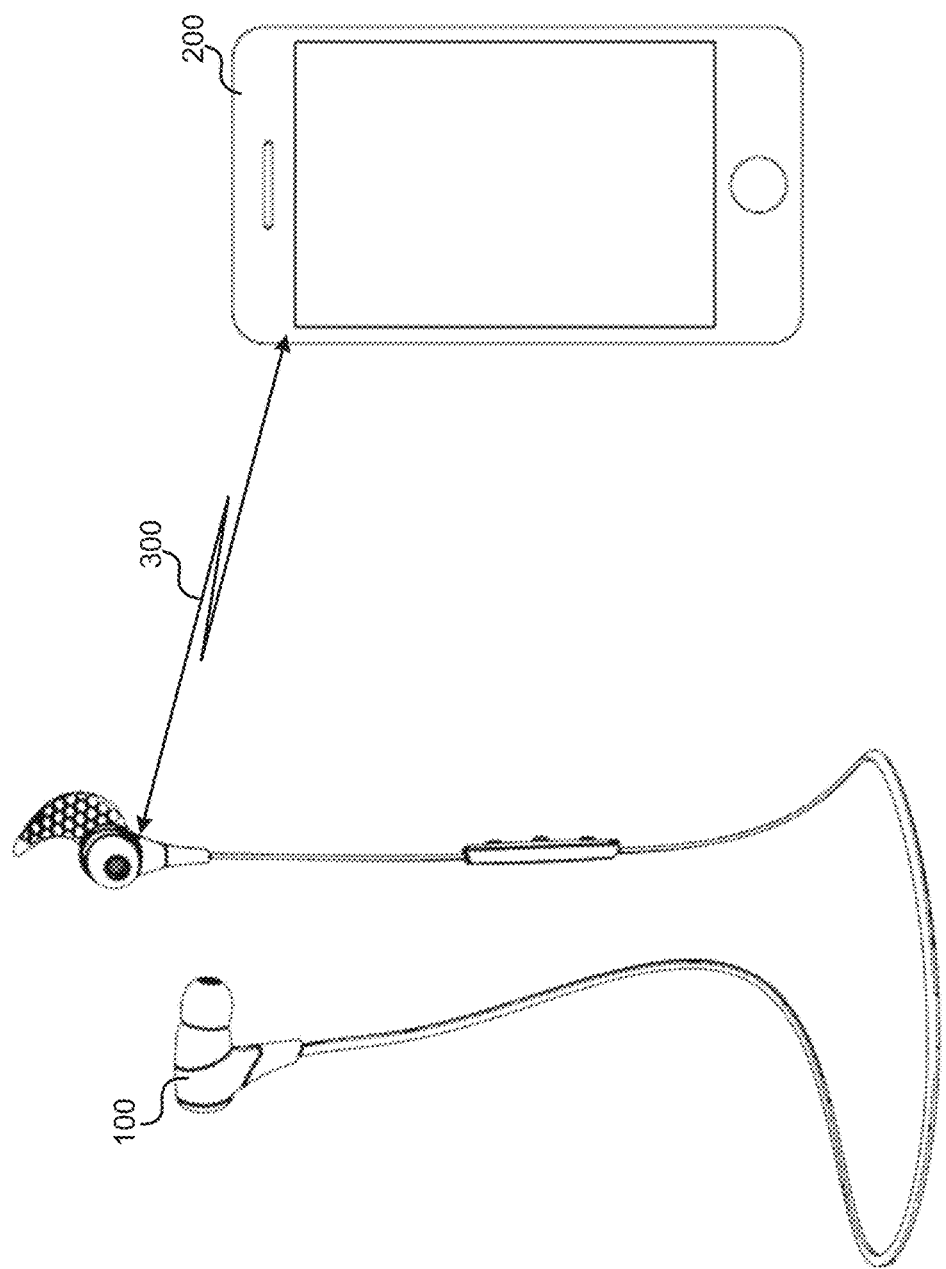
FIG. 1 illustrates an example communications environment in which embodiments of the disclosed technology may be implemented.

FIG. 1 illustrates an example communications environment in accordance with an embodiment of the technology disclosed herein. In this embodiment, earphones 100 communicate biometric and audio data with computing device 200 over a communication link 300. The biometric data is measured by one or more sensors (e.g., heart rate sensor, accelerometer, gyroscope) of earphones 100. Although a smartphone is illustrated, computing device 200 may comprise any computing device (smartphone, tablet, laptop, smartwatch, desktop, etc.) configured to transmit audio data to earphones 100, receive biometric data from earphones 100 (e.g., heartrate and motion data), and process the biometric data collected by earphones 100. In additional embodiments, computing device 200 itself may collect additional biometric information that is provided for display. For example, if computing device 200 is a smartphone it may use built in accelerometers, gyroscopes, and a GPS to collect additional biometric data.

Computing device 200 additionally includes a graphical user interface (GUI) to perform functions such as accepting user input and displaying processed biometric data to the user. The GUI may be provided by various operating systems known in the art, such as, for example, iOS, Android, Windows Mobile, Windows, Mac OS, Chrome OS, Linux, Unix, a gaming platform OS, etc. The biometric information displayed to the user can include, for example a summary of the user's activities, a summary of the user's fitness levels, activity recommendations for the day, the user's heart rate and heart rate variability (HRV), and other activity related information. User input that can be accepted on the GUI can include inputs for interacting with an activity tracking application further described below.

In preferred embodiments, the communication link 300 is a wireless communication link based on one or more wireless communication protocols such as BLUETOOTH, ZIGBEE, 802.11 protocols, Infrared (IR), Radio Frequency (RF), etc. Alternatively, the communications link 300 may be a wired link (e.g., using any one or a combination of an audio cable, a USB cable, etc.)

Figure 2A:
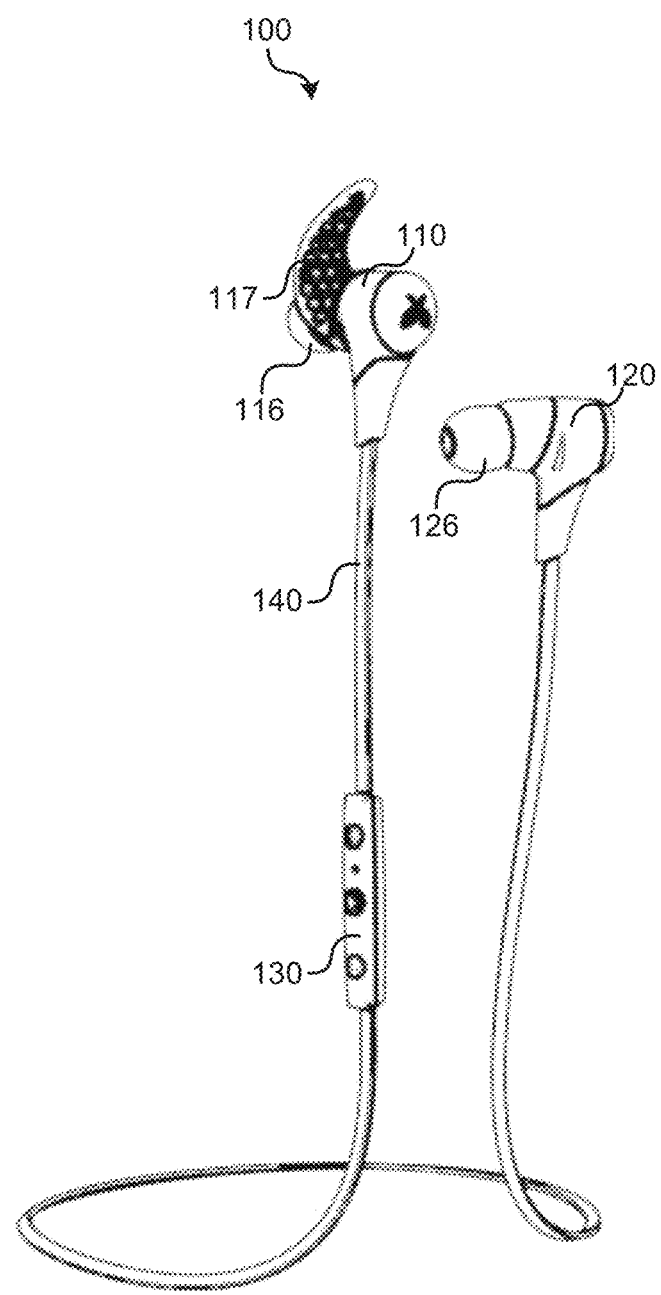
FIG. 2A illustrates a perspective view of exemplary earphones that may be used to implement the technology disclosed herein.

With specific reference now to earphones 100, FIG. 2A is a diagram illustrating a perspective view of exemplary earphones 100. FIG. 2A will be described in conjunction with FIG. 2B, which is a diagram illustrating an example architecture for circuitry of earphones 100. Earphones 100 comprise a left earphone 110 with tip 116, a right earphone 120 with tip 126, a controller 130 and a cable 140. Cable 140 electrically couples the right earphone 110 to the left earphone 120, and both earphones 110-120 to controller 130. Additionally, each earphone may optionally include a fin or ear cushion 117 that contacts folds in the outer ear anatomy to further secure the earphone to the wearer's ear.

In embodiments, earphones 100 may be constructed with different dimensions, including different diameters, widths, and thicknesses, in order to accommodate different human ear sizes and different preferences. In some embodiments of earphones 100, the housing of each earphone 110, 120 is rigid shell that surrounds electronic components. For example, the electronic components may include motion sensor 121, optical heartrate sensor 122, audio-electronic components such as drivers 113, 123 and speakers 114, 124, and other circuitry (e.g., processors 160, 165, and memories 170, 175). The rigid shell may be made with plastic, metal, rubber, or other materials known in the art. The housing may be cubic shaped, prism shaped, tubular shaped, cylindrical shaped, or otherwise shaped to house the electronic components.

The tips 116, 126 may be shaped to be rounded, parabolic, and/or semi-spherical, such that it comfortably and securely fits within a wearer's ear, with the distal end of the tip contacting an outer rim of the wearer's outer ear canal. In some embodiments, the tip may be removable such that it may be exchanged with alternate tips of varying dimensions, colors, or designs to accommodate a wearer's preference and/or fit more closely match the radial profile of the wearer's outer ear canal. The tip may be made with softer materials such as rubber, silicone, fabric, or other materials as would be appreciated by one of ordinary skill in the art.

In embodiments, controller 130 may provide various controls (e.g., buttons and switches) related to audio playback, such as, for example, volume adjustment, track skipping, audio track pausing, and the like. Additionally, controller 130 may include various controls related to biometric data gathering, such as, for example, controls for enabling or disabling heart rate and motion detection. In a particular embodiment, controller 130 may be a three button controller.

The circuitry of earphones 100 includes processors 160 and 165, memories 170 and 175, wireless transceiver 180, circuitry for earphone 110 and earphone 120, and a battery 190. In this embodiment, earphone 120 includes a motion sensor 121 (e.g., an accelerometer or gyroscope), an optical heartrate sensor 122, and a right speaker 124 and corresponding driver 123. Earphone 110 includes a left speaker 114 and corresponding driver 113. In additional embodiments, earphone 110 may also include a motion sensor (e.g., an accelerometer or gyroscope), and/or an optical heartrate sensor.

Figure 2B:
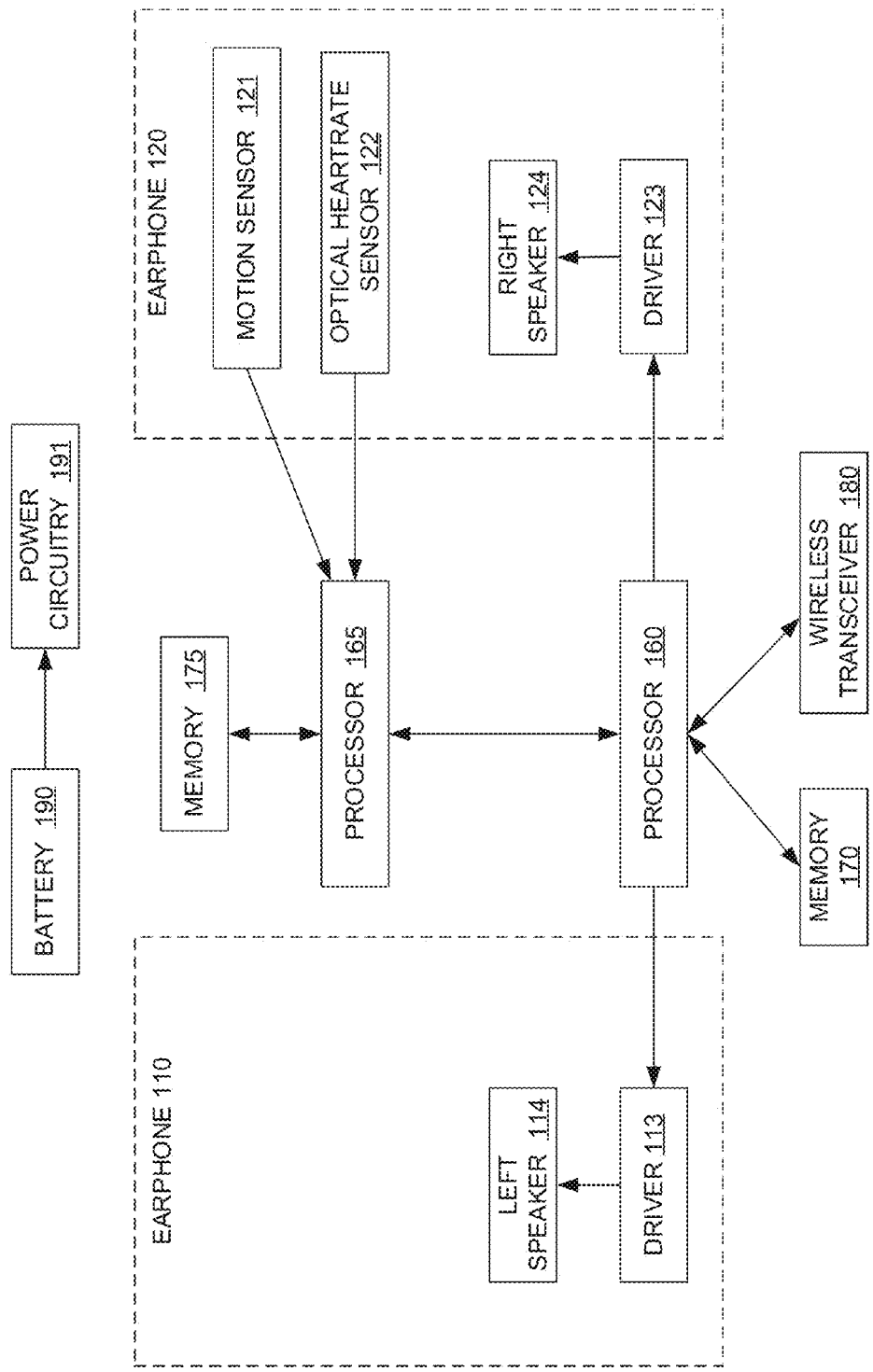
FIG. 2B illustrates an example architecture for circuitry of the earphones of FIG. 2A.

A biometric processor 165 comprises logical circuits dedicated to receiving, processing and storing biometric information collected by the biometric sensors of the earphones. More particularly, as illustrated in FIG. 2B, processor 165 is electrically coupled to motion sensor 121 and optical heartrate sensor 122, and receives and processes electrical signals generated by these sensors. These processed electrical signals represent biometric information such as the earphone wearer's motion and heartrate. Processor 165 may store the processed signals as biometric data in memory 175, which may be subsequently made available to a computing device using wireless transceiver 180. In some embodiments, sufficient memory is provided to store biometric data for transmission to a computing device for further processing.

During operation, optical heartrate sensor 122 uses a photoplethysmogram (PPG) to optically obtain the user's heart rate. In one embodiment, optical heartrate sensor 122 includes a pulse oximeter that detects blood oxygenation level changes as changes in coloration at the surface of a user's skin. More particularly, in this embodiment, the optical heartrate sensor 122 illuminates the skin of the user's ear with a light-emitting diode (LED). The light penetrates through the epidermal layers of the skin to underlying blood vessels. A portion of the light is absorbed and a portion is reflected back. The light reflected back through the skin of the user's ear is then obtained with a receiver (e.g., a photodiode) and used to determine changes in the user's blood oxygen saturation (SpO2) and pulse rate, thereby permitting calculation of the user's heart rate using algorithms known in the art (e.g., using processor 165). In this embodiment, the optical sensor may be positioned on one of the earphones such that it is proximal to the interior side of a user's tragus when the earphones are worn.

In various embodiments, optical heartrate sensor 122 may also be used to estimate a heart rate variable (HRV), i.e. the variation in time interval between consecutive heartbeats, of the user of earphones 100. For example, processor 165 may calculate the HRV using the data collected by sensor 122 based on a time domain methods, frequency domain methods, and other methods known in the art that calculate HRV based on data such as the mean heart rate, the change in pulse rate over a time interval, and other data used in the art to estimate HRV.

In further embodiments, logic circuits of processor 165 may further detect, calculate, and store metrics such as the amount of physical activity, sleep, or rest over a period of time, or the amount of time without physical activity over a period of time. The logic circuits may use the HRV, the metrics, or some combination thereof to calculate a recovery score. In various embodiments, the recovery score may indicate the user's physical condition and aptitude for further physical activity for the current day. For example, the logic circuits may detect the amount of physical activity and the amount of sleep a user experienced over the last 48 hours, combine those metrics with the user's HRV, and calculate a recovery score. In various embodiments, the calculated recovery score may be based on any scale or range, such as, for example, a range between 1 and 10, a range between 1 and 100, or a range between 0% and 100%.

During audio playback, earphones 100 wirelessly receive audio data using wireless transceiver 180. The audio data is processed by logic circuits of audio processor 160 into electrical signals that are delivered to respective drivers 113 and 123 of left speaker 114 and right speaker 124 of earphones 110 and 120. The electrical signals are then converted to sound using the drivers. Any driver technologies known in the art or later developed may be used. For example, moving coil drivers, electrostatic drivers, electret drivers, orthodynamic drivers, and other transducer technologies may be used to generate playback sound.

The wireless transceiver 180 is configured to communicate biometric and audio data using available wireless communications standards. For example, in some embodiments, the wireless transceiver 180 may be a BLUETOOTH transmitter, a ZIGBEE transmitter, a Wi-Fi transmitter, a GPS transmitter, a cellular transmitter, or some combination thereof. Although FIG. 2B illustrates a single wireless transceiver 180 for both transmitting biometric data and receiving audio data, in an alternative embodiment, a transmitter dedicated to transmitting only biometric data to a computing device may be used. In this alternative embodiment, the transmitter may be a low energy transmitter such as a near field communications (NFC) transmitter or a BLUETOOTH low energy (LE) transmitter. In implementations of this particular embodiment, a separate wireless receiver may be provided for receiving high fidelity audio data from an audio source. In yet additional embodiments, a wired interface (e.g., micro-USB) may be used for communicating data stored in memories 165 and 175.

FIG. 2B also shows that the electrical components of headphones 100 are powered by a battery 190 coupled to power circuitry 191. Any suitable battery or power supply technologies known in the art or later developed may be used. For example, a lithium-ion battery, aluminum-ion battery, piezo or vibration energy harvesters, photovoltaic cells, or other like devices can be used. In embodiments, battery 190 may be enclosed in earphone 110 or earphone 120. Alternatively, battery 102 may be enclosed in controller 130. In embodiments, the circuitry may be configured to enter a low-power or inactive mode when earphones 100 are not in use. For example, mechanisms such as, for example, an on/off switch, a BLUETOOTH transmission disabling button, or the like may be provided on controller 130 such that a user may manually control the on/off state of power-consuming components of earphones 100.

It should be noted that in various embodiments, processors 160 and 165, memories 170 and 175, wireless transceiver 180, and battery 190 may be enclosed in and distributed throughout any one or more of earphone 110, earphone 120, and controller 130. For example, in one particular embodiment, processor 165 and memory 175 may be enclosed in earphone 120 along with optical heartrate sensor 122 and motion sensor 121. In this particular embodiment, these four components are electrically coupled to the same printed circuit board (PCB) enclosed in earphone 120. It should also be noted that although audio processor 160 and biometric processor 165 are illustrated in this exemplary embodiment as separate processors, in an alternative embodiment the functions of the two processors may be integrated into a single processor.

FIG. 3A illustrates a perspective view of one embodiment of an earphone 120, including an optical heartrate sensor 122, in accordance with the technology disclosed herein. FIG. 3A will be described in conjunction with FIGS. 3B-3C, which are perspective views illustrating placement of heartrate sensor 122 when earphone 120 is worn in a user's ear 350. As illustrated, earphone 120 includes a body 125, tip 126, ear cushion 127, and an optical heartrate sensor 122. Optical heartrate sensor 122 protrudes from a frontal side of body 125, proximal to tip 126 and where the earphone's nozzle (not shown) is present. FIGS. 3B-3C illustrate the optical sensor and ear interface 340 when earphone 120 is worn in a user's ear 350. When earphone 120 is worn, optical heartrate sensor 122 is proximal to the interior side of a user's tragus 360.

In this embodiment, optical heartrate sensor 122 illuminates the skin of the interior side of the ear's tragus 360 with a light-emitting diode (LED). The light penetrates through the epidermal layers of the skin to underlying blood vessels. A portion of the light is absorbed and a portion is reflected back. The light reflected back through the skin is then obtained with a receiver (e.g., a photodiode) of optical heartrate sensor 122 and used to determine changes in the user's blood flow, thereby permitting measurement of the user's heart rate and HRV.

In various embodiments, earphones 100 may be dual-fit earphones shaped to comfortably and securely be worn in either an over-the-ear configuration or an under-the-ear configuration. The secure fit provided by such embodiments keeps the optical heartrate sensor 122 in place on the interior side of the ear's tragus 360, thereby ensuring accurate and consistent measurements of a user's heartrate.

Figure 3F:
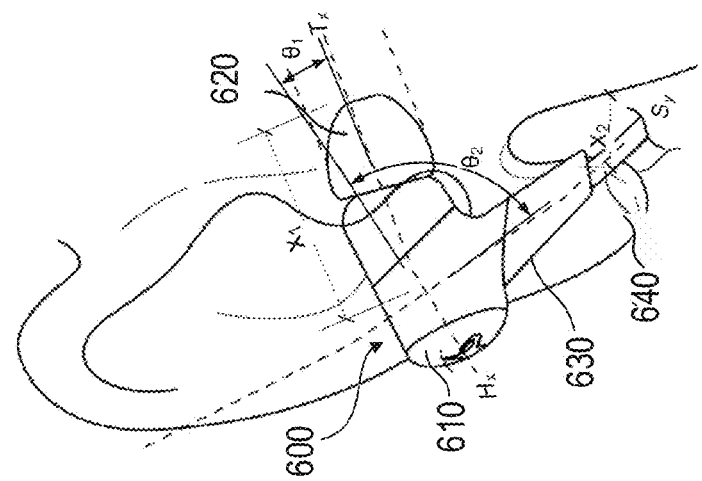
FIG. 3F illustrates a cross-sectional view of an under-the-ear configuration of the dual-fit earphones of FIG. 3D.
Figure 3E:
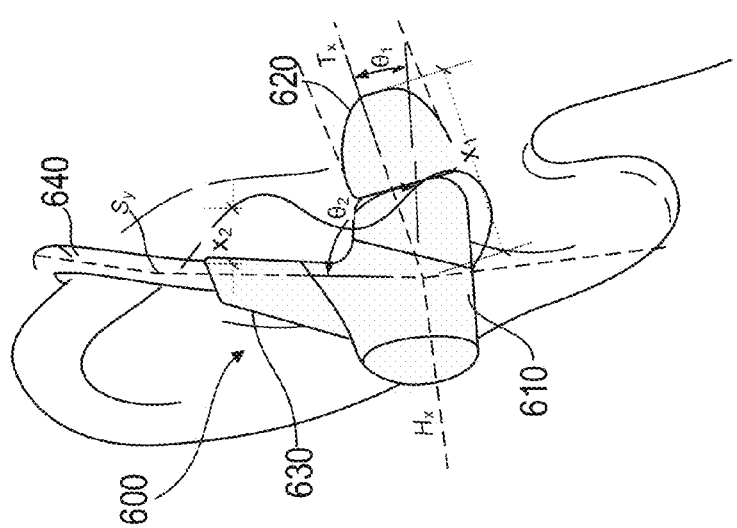
FIG. 3E illustrates a cross-sectional view of an over-the-ear configuration of the dual-fit earphones of FIG. 3D.
Figure 3D:
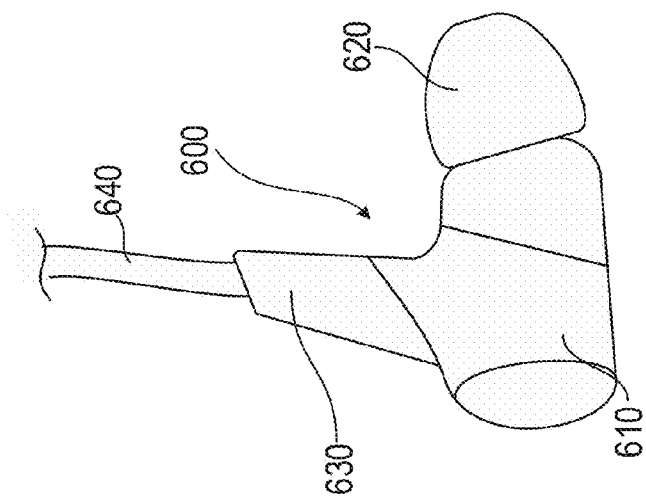
FIG. 3D illustrates a cross-sectional view of an over-the-ear configuration of dual-fit earphones in accordance with the disclosed technology.

FIGS. 3D and 3E are cross-sectional views illustrating one such embodiment of dual-fit earphones 600 being worn in an over-the-ear configuration. FIG. 3F illustrates dual-fit earphones 600 in an under-the-ear configuration.

As illustrated, earphone 600 includes housing 610, tip 620, strain relief 630, and cord or cable 640. The proximal end of tip 620 mechanically couples to the distal end of housing 610. Similarly, the distal end of strain relief 630 mechanically couples to a side (e.g., the top side) of housing 610. Furthermore, the distal end of cord 640 is disposed within and secured by the proximal end of strain relief 630. The longitudinal axis of the housing, $H_x$, forms angle $\theta_1$ with respect to the longitudinal axis of the tip, $T_x$. The longitudinal axis of the strain relief, $S_y$, aligns with the proximal end of strain relief 630 and forms angle $\theta_2$ with respect to the axis $H_x$. In several embodiments, $\theta_1$ is greater than 0 degrees (e.g., $T_x$ extends in a non-straight angle from $H_x$, or in other words, the tip 620 is angled with respect to the housing 610). In some embodiments, $\theta_1$ is selected to approximate the ear canal angle of the wearer. For example, $\theta_1$ may range between 5 degrees and 15 degrees. Also in several embodiments, $\theta_2$ is less than 90 degrees (e.g., $S_y$ extends in a non-orthogonal angle from $H_x$, or in other words, the strain relief 630 is angled with respect to a perpendicular orientation with housing 610). In some embodiments, $\theta_2$ may be selected to direct the distal end of cord 640 closer to the wearer's ear. For example, $\theta_2$ may range between 75 degrees and 89 degrees.

As illustrated, $x_1$ represents the distance between the distal end of tip 620 and the intersection of strain relief longitudinal axis $S_y$ and housing longitudinal axis $H_x$. One of skill in the art would appreciate that the dimension $x_1$ may be selected based on several parameters, including the desired fit to a wearer's ear based on the average human ear anatomical dimensions, the types and dimensions of electronic components (e.g., optical sensor, motion sensor, processor, memory, etc.) that must be disposed within the housing and the tip, and the specific placement of the optical sensor. In some examples, $x_1$ may be at least 18 mm. However, in other examples, $x_1$ may be smaller or greater based on the parameters discussed above.

Similarly, as illustrated, $x_2$ represents the distance between the proximal end of strain relief 630 and the surface wearer's ear. In the configuration illustrated, $\theta_2$ may be selected to reduce $x_2$, as well as to direct the cord 640 towards the wearer's ear, such that cord 640 may rest in the crevice formed where the top of the wearer's ear meets the side of the wearer's head. In some embodiments, $\theta_2$ may range between 75 degrees and 85 degrees. In some examples, strain relief 630 may be made of a flexible material such as rubber, silicone, or soft plastic such that it may be further bent towards the wearer's ear. Similarly, strain relief 630 may comprise a shape memory material such that it may be bent inward and retain the shape. In some examples, strain relief 630 may be shaped to curve inward towards the wearer's ear.

In some embodiments, the proximal end of tip 620 may flexibly couple to the distal end of housing 610, enabling a wearer to adjust $\theta_1$ to most closely accommodate the fit of tip 620 into the wearer's ear canal (e.g., by closely matching the ear canal angle).

Figures 4A, 4B:
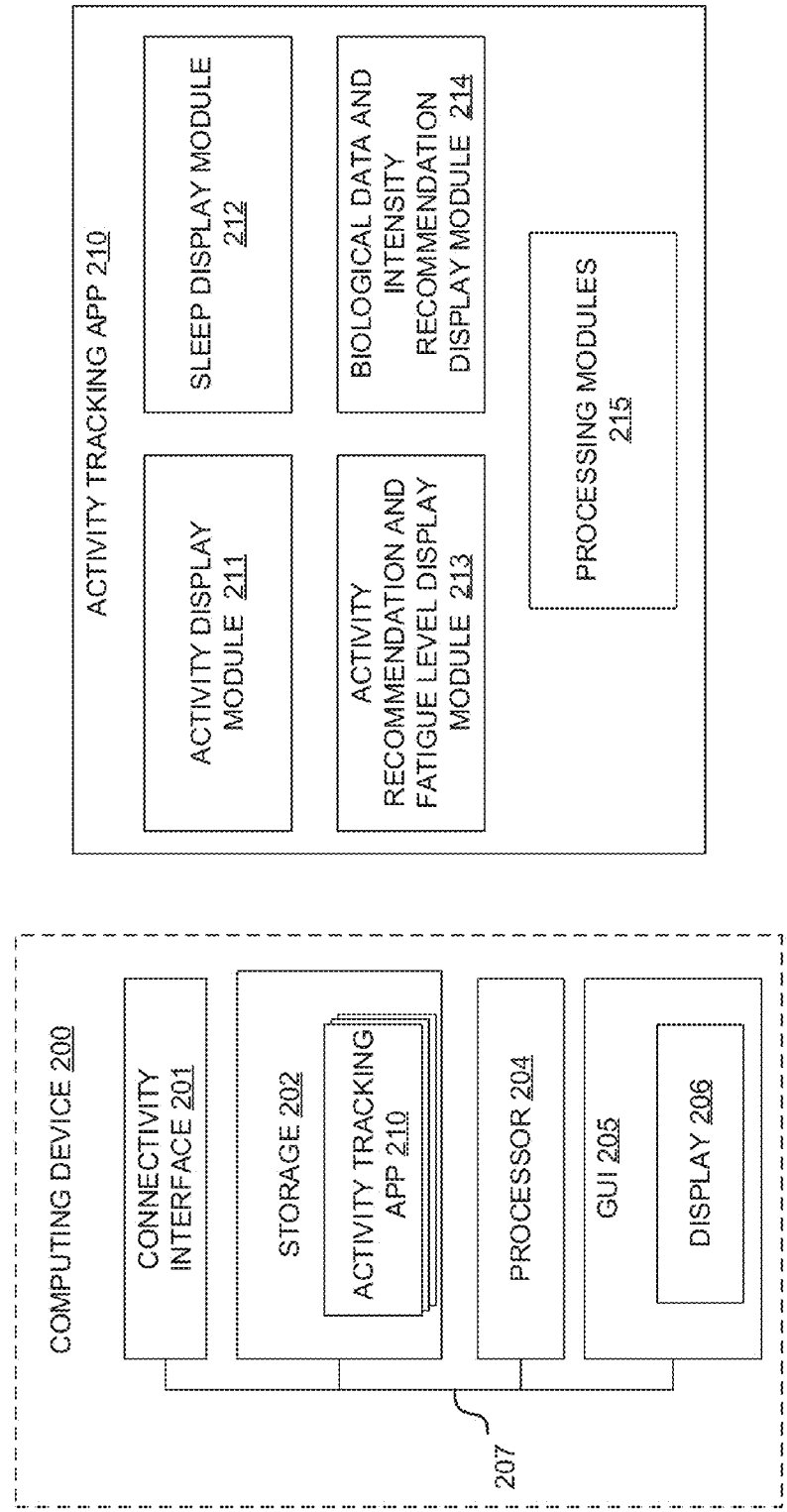
FIG. 4A is a block diagram illustrating an example computing device that may be used to implement embodiments of the disclosed technology.
FIG. 4B illustrates modules of an example activity monitoring application that may be used to implement embodiments of the disclosed technology.

As one having skill in the art would appreciate from the above description, earphones 100 in various embodiments may gather biometric user data that may be used to track a user's activities and activity level. That data may then be made available to a computing device, which may provide a GUI for interacting with the data using a software activity tracking application installed on the computing device. FIG. 4A is a block diagram illustrating example components of one such computing device 200 including an installed activity tracking application 210.

As illustrated in this example, computing device 200 comprises a connectivity interface 201, storage 202 with activity tracking application 210, processor 204, a graphical user interface (GUI) 205 including display 206, and a bus 207 for transferring data between the various components of computing device 200.

Connectivity interface 201 connects computing device 200 to earphones 100 through a communication medium. The medium may comprise a wireless network system such as a BLUETOOTH system, a ZIGBEE system, an Infrared (IR) system, a Radio Frequency (RF) system, a cellular network, a satellite network, a wireless local area network, or the like. The medium may additionally comprise a wired component such as a USB system.

Storage 202 may comprise volatile memory (e.g. RAM), non-volatile memory (e.g. flash storage), or some combination thereof. In various embodiments, storage 202 may store biometric data collected by earphones 100. Additionally, storage 202 stores an activity tracking application 210, that when executed by processor 204, allows a user to interact with the collected biometric information.

In various embodiments, a user may interact with activity tracking application 210 via a GUI 205 including a display 206, such as, for example, a touchscreen display that accepts various hand gestures as inputs. In accordance with various embodiments, activity tracking application 210 may process the biometric information collected by earphones 100 and present it via display 206 of GUI 205. Before describing activity tracking application 210 in further detail, it is worth noting that in some embodiments earphones 100 may filter the collected biometric information prior to transmitting the biometric information to computing device 200. Accordingly, although the embodiments disclosed herein are described with reference to activity tracking application 210 processing the received biometric information, in various implementations various preprocessing operations may be performed by a processor 160, 165 of earphones 100.

In various embodiments, activity tracking application 210 may be initially configured/setup (e.g., after installation on a smartphone) based on a user's self-reported biological information, sleep information, and activity preference information. For example, during setup a user may be prompted via display 206 for biological information such as the user's gender, height, age, and weight. Further, during setup the user may be prompted for sleep information such as the amount of sleep needed by the user and the user's regular bed time. Further, still, the user may be prompted during setup for a preferred activity level and activities the user desires to be tracked (e.g., running, walking, swimming, biking, etc.) In various embodiments, described below, this self-reported information may be used in tandem with the information collected by earphones 100 to display activity monitoring information using various modules.

Following setup, activity tracking application 210 may be used by a user to monitor and define how active the user wants to be on a day-to-day basis based on the biometric information (e.g., accelerometer information, optical heart rate sensor information, etc.) collected by earphones 100. As illustrated in FIG. 4B, activity tracking application 210 may comprise various display modules, including an activity display module 211, a sleep display module 212, an activity recommendation and fatigue level display module 213, and a biological data and intensity recommendation display module 214. Additionally, activity tracking application 210 may comprise various processing modules 215 for processing the activity monitoring information (e.g., optical heart-rate information, accelerometer information, gyroscope information, etc.) collected by the earphones or the biological information entered by the users. These modules may be implemented separately or in combination. For example, in some embodiments activity processing modules 215 may be directly integrated with one or more of display modules 211-214.

As will be further described below, each of display modules 211-214 may be associated with a unique display provided by activity tracking app 210 via display 206. That is, activity display module 211 may have an associated activity display, sleep display module 212 may have an associated sleep display, activity recommendation and fatigue level display module 213 may have an associated activity recommendation and fatigue level display, and biological data and intensity recommendation display module 214 may have an associated biological data and intensity recommendation display.

Figure 5:
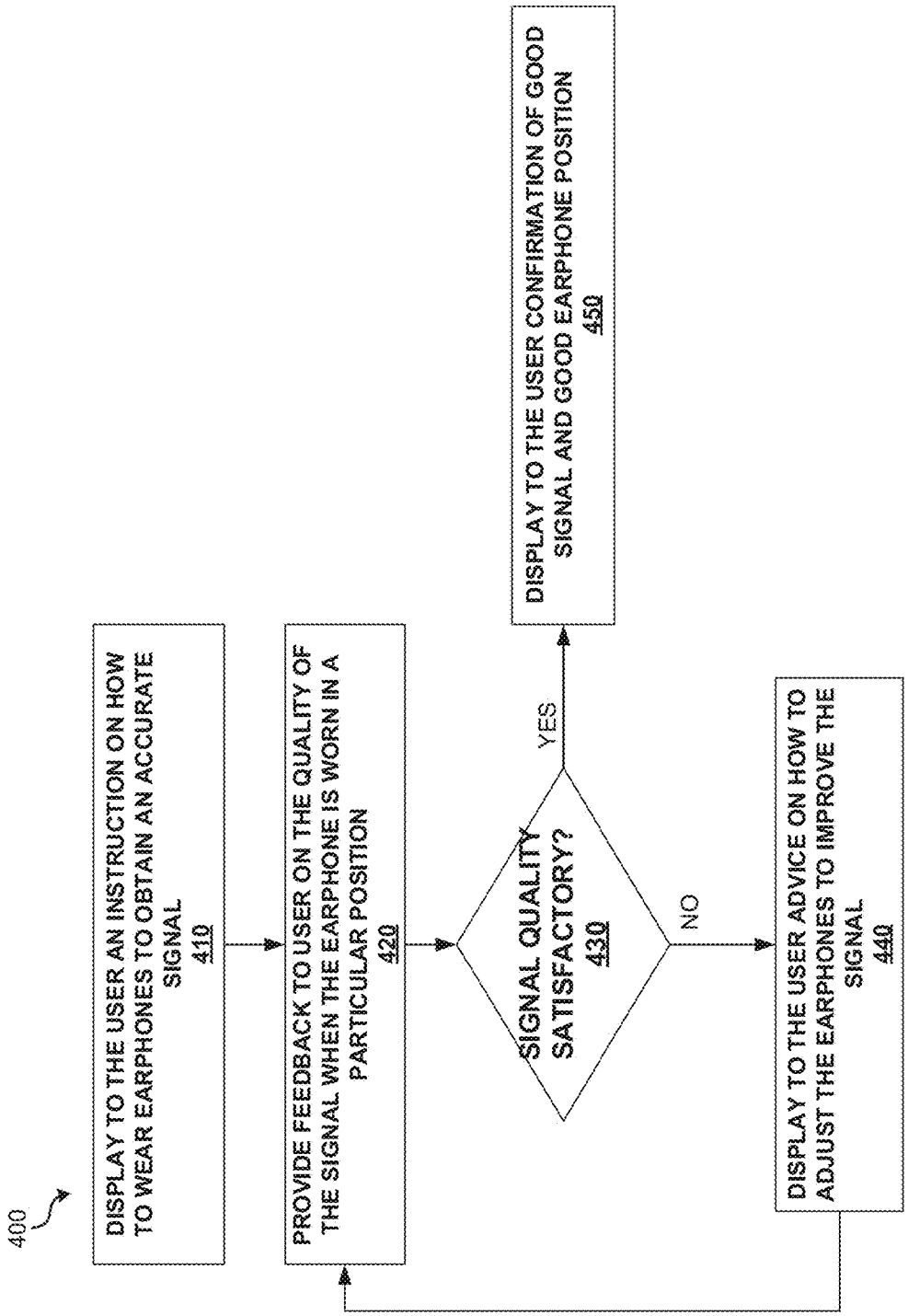
FIG. 5 is an operational flow diagram illustrating a method of prompting a user to adjust the placement of earphones in the user's ear to ensure accurate biometric data collection by the earphones' biometric sensors.

In embodiments, application 210 may be used to display to the user an instruction for wearing and/or adjusting earphones 100 if it is determined that optical heartrate sensor 122 and/or motion sensor 121 are not accurately gathering motion data and heart rate data. FIG. 5 is an operational flow diagram illustrating one such method 400 of an earphone adjustment feedback loop with a user that ensures accurate biometric data collection by earphones 100. At operation 410, execution of application 210 may cause display 206 to display an instruction to the user on how to wear earphones 100 to obtain an accurate and reliable signal from the biometric sensors. In embodiments, operation 410 may occur once after installing application 210, once a day (e.g., when user first wears the earphones 100 for the day), or at any customizable and/or predetermined interval.

At operation 420, feedback is displayed to the user regarding the quality of the signal received from the biometric sensors based on the particular position that earphones 100 are being worn. For example, display 206 may display a signal quality bar or other graphical element. At decision 430, it is determined if the biosensor signal quality is satisfactory for biometric data gathering and use of application 210. In various embodiments, this determination may be based on factors such as, for example, the frequency with which optical heartrate sensor 122 is collecting heart rate data, the variance in the measurements of optical heartrate sensor 122, dropouts in heart rate measurements by sensor 122, the signal-to-noise ratio approximation of optical heartrate sensor 122, the amplitude of the signals generated by the sensors, and the like.

If the signal quality is unsatisfactory, at operation 440, application 210 may cause display 206 to display to the user advice on how to adjust the earphones to improve the signal, and operations 420 and decision 430 may subsequently be repeated. For example, advice on adjusting the strain relief of the earphones may be displayed. Otherwise, if the signal quality is satisfactory, at operation 450, application may cause display 206 to display to the user confirmation of good signal quality and/or good earphone position. Subsequently, application 210 may proceed with normal operation (e.g., display modules 211-214).

Figure 6:
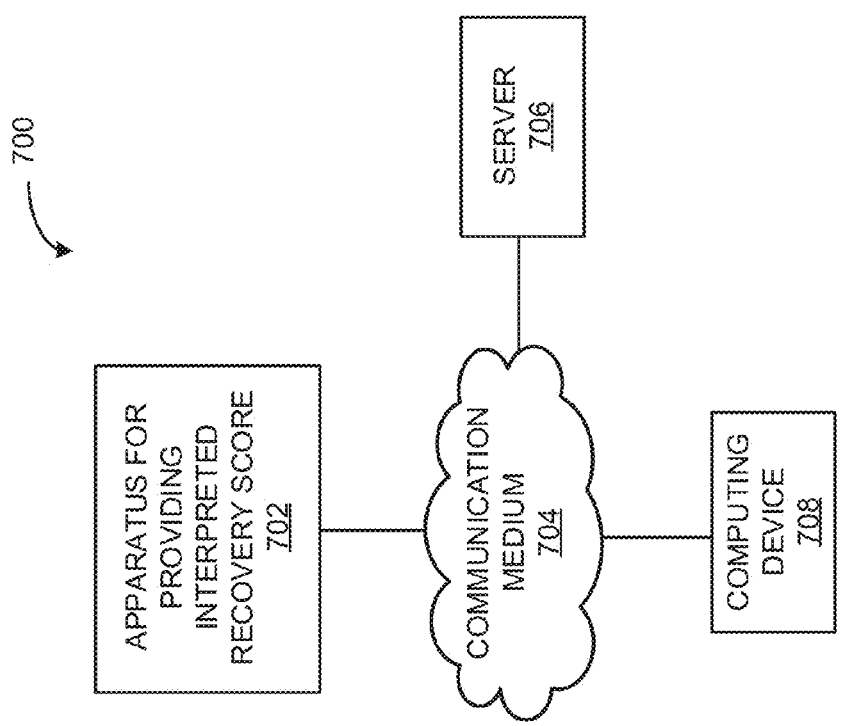
FIG. 6 illustrates an example system for providing an interpreted recovery score.

In various embodiments, earphones 100 and computing device 200 may be implemented in a system for providing an interpreted recovery score. FIG. 6 is a schematic block diagram illustrating an example system 700 for providing an interpreted recovery score. System 700 includes an apparatus for providing an interpreted recovery score 702 (e.g., computing device 200), communication medium 704, server 706, and computing device 708 (e.g., earphones 100).

Communication medium 704 may be implemented in a variety of forms. For example, communication medium 704 may be an Internet connection, such as a local area network ("LAN"), a wide area network ("WAN"), a fiber optic network, internet over power lines, a hard-wired connection (e.g., a bus), and the like, or any other kind of network connection. Communication medium 704 may be implemented using any combination of routers, cables, modems, switches, fiber optics, wires, radio, and the like. Communication medium 704 may be implemented using various wireless standards, such as BLUETOOTH, Wi-Fi, LTE, etc.

Server 706 directs communications made over communication medium 704. Server 706 may be, for example, an Internet server, a router, a desktop or laptop computer, a smartphone, a tablet, a processor, a module, or the like. In one embodiment, server 706 directs communications between communication medium 704 and computing device 708. For example, server 706 may update information stored on computing device 708, or server 706 may send information to computing device 708 in real time.

Computing device 708 may take a variety of forms, such as a desktop or laptop computer, a smartphone, a tablet, a processor, a module, or the like. In addition, computing device 708 may be a module, processor, and/or other electronics embedded in a wearable device such as earphones, a bracelet, a smartwatch, a piece of clothing, and so forth. For example, computing device 708 may be substantially similar to electronics embedded in earphones 100. Computing device 708 may communicate with other devices over communication medium 704 with or without the use of server 706. In one embodiment, computing device 708 includes apparatus 702. In various embodiments, apparatus 702 may be used to perform various processes described herein.

Figure 7:
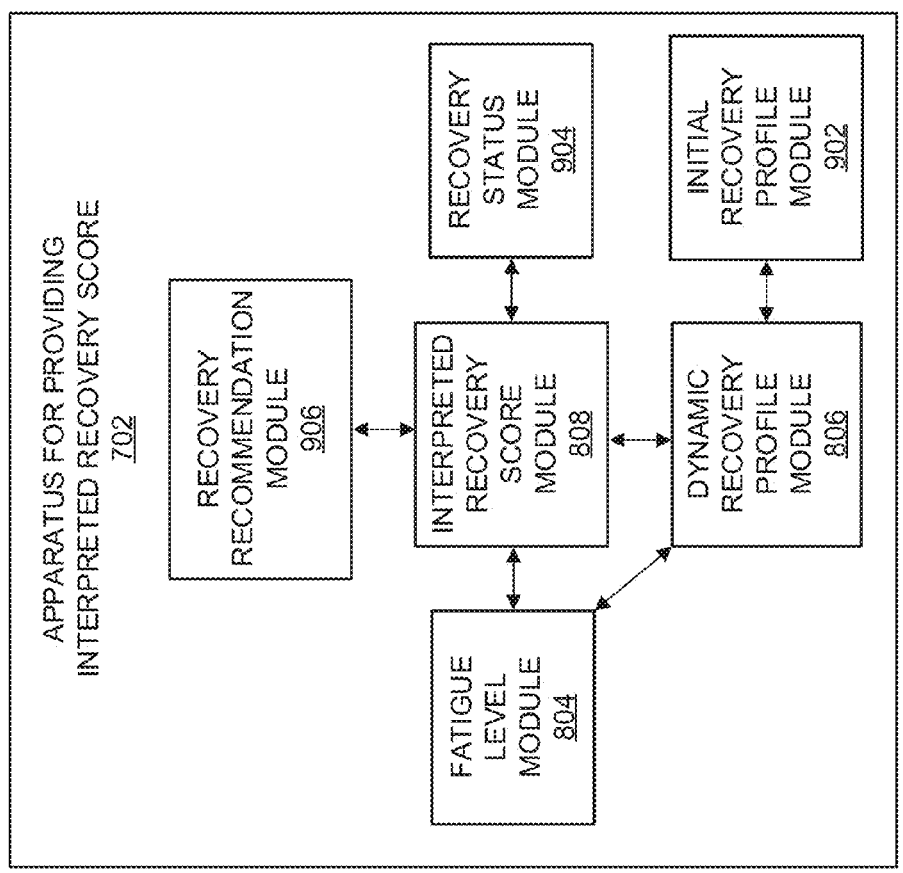
FIG. 7 illustrates an example apparatus for providing an interpreted recovery score.

FIG. 7 is a schematic block diagram illustrating an embodiment of an apparatus 702 for providing an interpreted recovery score. As illustrated in this particular embodiment, apparatus 702 includes fatigue level module 804, dynamic recovery profile module 806, interpreted recovery score module 808, initial recovery profile module 902, recovery status module 904, and recovery recommendation module 906. In one embodiment of apparatus 702, a movement monitoring module (not shown) monitors a movement to create a metabolic activity score based on the movement and user information. The movement monitoring module will be described below in further detail with regard to various processes.

Fatigue level module 804 detects a fatigue level. Dynamic recovery profile module 806 creates and updates a dynamic recovery profile based on an archive. The archive includes historical information about the fatigue level. In one embodiment, the archive includes historical information about the movement and the metabolic activity score. Interpreted recovery score module 808 creates and updates an interpreted recovery score based on the fatigue level and the dynamic recovery profile.

Fatigue level module 804, dynamic recovery profile module 806, interpreted recovery score module 808, initial recovery profile module 902, recovery status module 904, and recovery recommendation module 906 will be described below in further detail with regard to various processes.

In one embodiment, at least one of fatigue level module 804, dynamic recovery profile module 806, interpreted recovery score module 808, initial recovery profile module 902, recovery status module 904, and recovery recommendation module 906 is embodied in earphones 100. In various embodiments, any of the modules described herein may be embodied in earphones 100 and connect to other modules described herein via communication medium 704. In other cases, the modules are embodiment in various other forms of hardware and/or software.

Figure 8A:
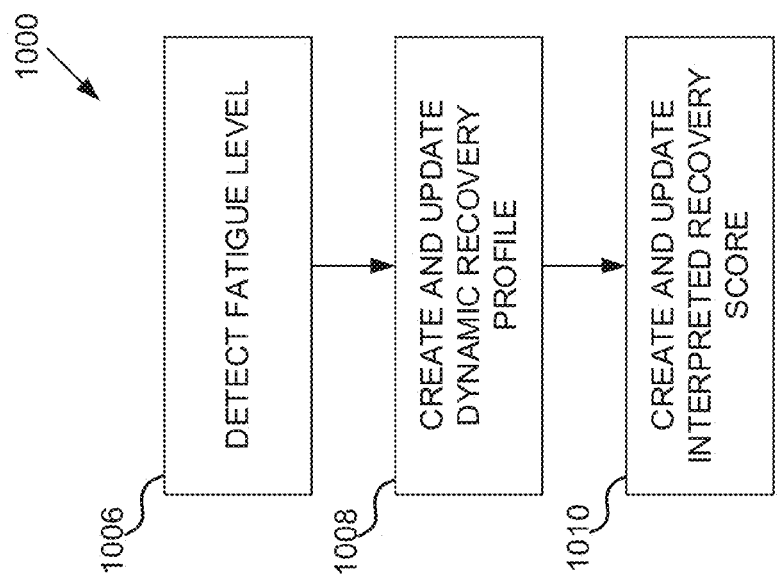
FIG. 8A is an operational flow diagram illustrating an example method for creating and updating an interpreted recovery score.

FIG. 8A is an operational flow diagram illustrating an example method 1000 for providing an interpreted recovery score in accordance with an embodiment of the present disclosure. The operations of method 1000 create and update an interpreted recovery score based on a user's personalized fatigue levels, as recorded over time. In various embodiments, the fatigue level is based on a measured heart rate variability for the user and is a function of recovery. Moreover, the operations of method 1000 take into account not only the user's current fatigue level, but also the relationship between current and past fatigue levels to create an interpreted recovery score that accurately reflects the user's physical condition and performance capabilities. This aids in providing a personalized metric by which the user can attain peak performance. In one embodiment, apparatus 702 and earphones 100 perform various operations of method 1000.

In one embodiment, movement is monitored to create a metabolic activity score based on the movement and user information. The metabolic activity score, in one embodiment, is created from a set of metabolic loadings. The metabolic loadings may be determined by identifying a user activity type from a set of reference activity types and by identifying a user activity intensity from a set of reference activity intensities. In addition, the metabolic loadings may be determined based on information provided by a user (user information).

User information may include, for example, an individual's height, weight, age, gender, geographic and environmental conditions, and the like. The user may provide the user information by, for example, a user interface of computing device 708 and/or apparatus 702 (e.g., using application 210 and GUI 205). User information may be determined based on various measurements—for example, measurements of the user's body-fat content or body type. In addition, the user information may be determined by an altimeter or GPS, which may be used to determine the user's elevation, weather conditions in the user's environment, etc. In one embodiment, apparatus 702 obtains user information from the user indirectly. For example, apparatus 702 may collect the user information from a social media account, from a digital profile, or the like.

The user information, in one embodiment, includes a user lifestyle selected from a set of reference lifestyles. For example, apparatus 702, may prompt the user for information about the user's lifestyle (e.g., via a user interface provided by application 210). By way of example, apparatus 702 may prompt the user to determine how active the user's lifestyle is. Additionally, the user may be prompted to select the user lifestyle from the set of reference lifestyles. The reference lifestyles may include a range of lifestyles, for example, ranging from inactive, on one end, to highly active on the other end. In such a case, the set of reference lifestyles may include sedentary, mildly active, moderately active, and heavily active.

In one instance, the user lifestyle is determined from the user as an initial matter. For example, upon initiation, apparatus 702 may prompt the user to provide the user lifestyle. In a further embodiment, the user is prompted periodically to select the user lifestyle. In this fashion, the user lifestyle selected may be aligned with the user's actual activity level as the user's activity level varies over time. In another embodiment, the user lifestyle is updated without intervention from the user.

The metabolic loadings, in one embodiment, are numerical values and may represent a rate of calories burned per unit weight per unit time (e.g., having units of kcal per kilogram per hour). By way of example, the metabolic loadings may also be represented in units of oxygen uptake (e.g., in milliliters per kilogram per minute). In addition, the metabolic loadings may represent a ratio of the metabolic rate during activity (e.g., the metabolic rate associated with a particular activity type and/or activity intensity) to the metabolic rate during rest. The metabolic loadings, in one embodiment, are represented in a metabolic table, such as metabolic table 1050, illustrated in FIG. 8B. In one illustrative case, the metabolic loadings are specific to the user information. For example, the metabolic loadings may increase for a heavier user, or for an increased elevation, but may decrease for a lighter user or for a decreased elevation.

In one embodiment, the set of metabolic loadings is determined based on the user lifestyle, in addition to the other user information. For example, the metabolic loadings for a user with a heavily active lifestyle may differ from the metabolic loadings for a user with a sedentary lifestyle. In this fashion, there may be a greater coupling between the metabolic loadings and the user's characteristics.

In various embodiments, a computing device 708 (e.g., earphones 100) stores or provides the metabolic loadings. Moreover, the metabolic loadings may be maintained or provided by server 706 or over communication medium 704. In one embodiment, a system administrator provides the metabolic loadings based on a survey, publicly available data, scientifically determined data, compiled user data, or any other source of data. In some instances, a movement monitoring module performs the above-described operations. In various embodiments, the movement monitoring module includes a metabolic loading module and a metabolic table module that determine the metabolic loading associated with the movement.

In one embodiment, a metabolic table is maintained based on the user information. The metabolic table may include metabolic loadings, which may be based on the user information. In some cases, the metabolic table is maintained based on standard user information, in place of or in addition to the user information. The standard user information may comprise, for example, the average fitness characteristics of all individuals being the same age as the user, the same height as the user, etc. In another embodiment, instead of maintaining the metabolic table based on standard information, if the user has not provided user information, maintaining the metabolic table is delayed until the user information is obtained.

Figure 8B:
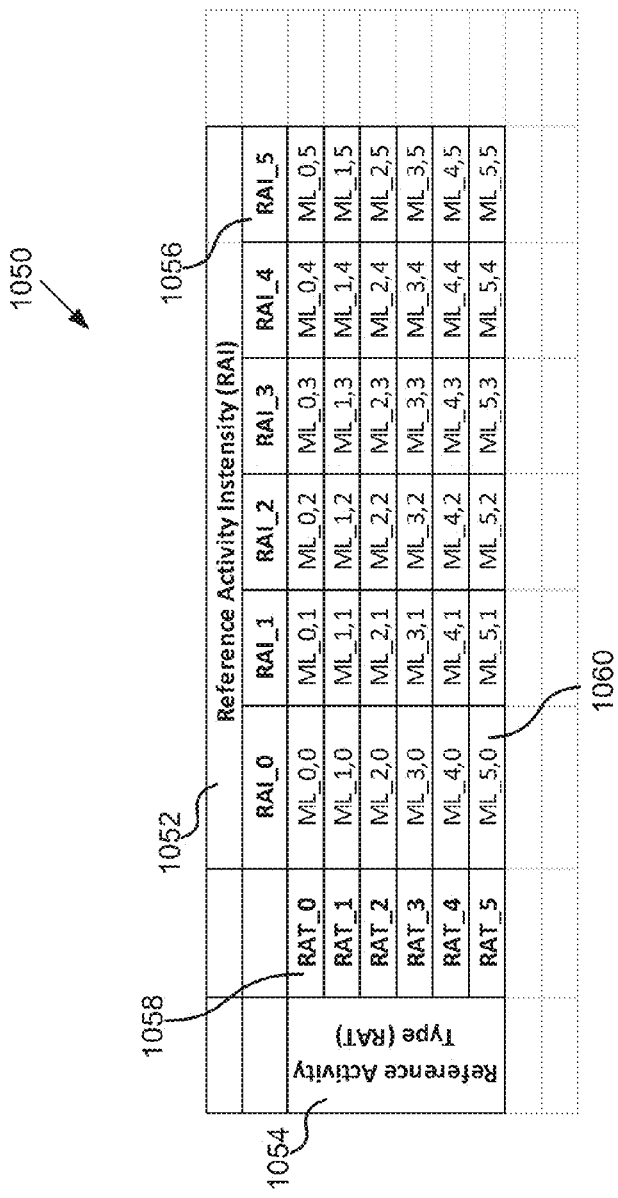
FIG. 8B is an example metabolic loading table

As illustrated in FIG. 8B, in one embodiment, the metabolic table is maintained as metabolic table 1050. Metabolic table 1050 may be stored in a storage of computing device 708 (e.g., memories 170, 175) or apparatus 702 (e.g., storage 202), and may include information such as reference activity types (RATs) 1054, reference activity intensities (RAIs) 1052, and/or metabolic loadings (MLs) 1060. As illustrated in FIG. 10B, in one embodiment, RATs 1054 are arranged as rows 1058 in metabolic table 1050. Each of a set of rows 1058 corresponds to different RATs 1054, and each row 1058 is designated by a row index number. For example, the first RAT row 1058 may be indexed as RAT_0, the second as RAT_1, and so on for as many rows as metabolic table 1050 may include.

The reference activity types may include typical activities, such as running, walking, sleeping, swimming, bicycling, skiing, surfing, resting, working, and so on. The reference activity types may also include a catch-all category, for example, general exercise. The reference activity types may also include atypical activities, such as skydiving, SCUBA diving, and gymnastics. In one embodiment, the user defines a user-defined activity by programming computing device 708 or apparatus 702 (e.g., using application 210) with information about the user-defined activity, such as pattern of movement, frequency of pattern, and intensity of movement. The typical reference activities may be provided, for example, by metabolic table 1050.

In one embodiment, reference activity intensities 1052 are arranged as columns 1056 in metabolic table 1050, with each column 1056 corresponding to different RAIs 1052. Each column 1056 is designated by a different column index number. For example, the first RAI column 1056 is indexed as RAI_0, the second as RAI_1 and so on for as many columns 1056 as metabolic table 1050 may include.

The reference activity intensities include, in one embodiment, a numeric scale. By way of example, the reference activity intensities may include numbers ranging from one to ten (representing increasing activity intensity). The reference activities may also be represented as a range of letters, colors, and the like. The reference activity intensities may be associated with the vigorousness of an activity. For example, the reference activity intensities may represented by ranges of heart rates or breathing rates.

In one embodiment, metabolic table 1050 includes metabolic loadings 1060. Each metabolic loading 1060 corresponds to a reference activity type 1058 of the reference activity types 1054 and a reference activity intensity 1056 of the reference activity intensities 1052. Each metabolic loading 1060 corresponds to a unique combination of reference activity type 1054 and reference activity intensity 1052. For example, in the column and row arrangement discussed above, one of the reference activity types 1054 of a series of rows 1058 of reference activity types, and one of the reference activity intensities 1052 of a series of columns 1056 of reference activity intensities correspond to a particular metabolic loading 1060. In such an arrangement, each metabolic loading 1060 is identifiable by only one combination of reference activity type 1058 and reference activity intensity 1056.

This concept is illustrated in FIG. 8B. As shown, each metabolic loading 1060 is designated using a two-dimensional index, with the first index dimension corresponding to the row 1058 number and the second index dimension corresponding to the column 1056 number of the metabolic loading 1060. For example, in FIG. 8B, ML_2,3 has a first dimension index of 2 and a second dimension index of 3. ML_2,3 corresponds to the row 1058 for RAT_2 and the column 1056 for RAI_3. Any combination of RAT_M and RAI_N may identify a corresponding ML_M,N in metabolic table 1050, where M is any number corresponding to a row 1058 number in metabolic table 1050 and N is any number corresponding to a column 1056 number in metabolic table 1050. By way of example, the reference activity type RAT_3 may be "surfing," and the reference activity intensity RAI_3 may be "4." This combination in metabolic table 1050 corresponds to metabolic loading 1060 ML_3,3, which may, for example, represent 5.0 kcal/kg/hour (a typical value for surfing). In various embodiments, some of the above-described operations are performed by movement monitoring module 802 and some of the operations are performed by a metabolic table module.

Referring again to method 1000, in various embodiments, the movement is monitored by location tracking (e.g., Global Positioning Satellites (GPS) or by a location-tracking device connected to a network via communication medium 704). The general location of the user, as well as specific movements of the user's body, are monitored. For example, the movement of the user's leg in x, y, and z directions may be monitored using a motion sensor (e.g., by an accelerometer or gyroscope). In one embodiment, apparatus 702 receives an instruction regarding which body part is being monitored. For example, apparatus 702 may receive an instruction that the movement of a user's head, wrist, ankle, or torso is being monitored.

In various embodiments, the movement of the user is monitored and a pattern of the movement (pattern) is determined. The pattern may be detected by a motion sensor (e.g., accelerometer or gyroscope). The pattern may be a repetition of a motion or a similar motion monitored by the method 1000. For example, the pattern may be geometric shape (e.g., a circle, line, oval) of repeated movement that is monitored. In some cases, the repetition of the motion in the geometric shape is not repeated consistently over time, but is maintained for a substantial proportion of the repetitions of the movement. For instance, one pattern of elliptical motion in a repetitive pattern of ten circular motions may be monitored, and the pattern may be determined to be circular.

In further embodiments, the geometric shape of the pattern of movement is a three dimensional (3-D) shape. To illustrate, the pattern associated with the head of a person swimming freestyle may be monitored and analyzed as a geometric shape in three dimensions. The pattern may be described in a form that can be recognized using method 1000. Such a form may include computer code that describes the spatial relationship of a set of points, along with changes in acceleration forces that are experienced along those points as, for example, a sensor travels through the pattern's trajectory.

In various embodiments, monitoring the pattern includes monitoring the frequency with which the pattern is repeated, i.e., the pattern frequency. The pattern frequency may be derived from a repetition period of the pattern, i.e., the pattern repetition period. The pattern repetition period may be the length of time elapsing from when a device or sensor passes through a certain point in a pattern and when the device or sensor returns to that point when the pattern is repeated. For example, the sensor may be at point x, y, z at time t_0. The device may then move along the trajectory of the pattern, eventually returning to point x, y, z at time_1. The pattern repetition period would be the difference between t_1 and t_0 (e.g., measured in seconds). The pattern frequency may be the reciprocal of the pattern repetition period, and may have units of cycles per second. When the pattern repetition period is, for example, two seconds, the pattern frequency would be 0.5 cycles per second.

In some embodiments, various other inputs are used to determine the activity type and activity intensity. For example, monitoring the movement may include monitoring the velocity at which the user is moving (or the user velocity). The user velocity may have units of kilometers per hour. In one embodiment, the user's location information is monitored to determine the user velocity. This may be done by GPS, through communication medium 704, and so on. The user velocity may be distinguished from the speed of the pattern (or pattern speed). For example, the user may be swimming at a user velocity of 5 km/hour, but the pattern speed of the user's head may be 2 km/hour at a given point (e.g., as the head rotates between swimming strokes). The pattern speed may be monitored using, for example, an accelerometer or gyroscope.

In one embodiment, the user's altitude is monitored. This may be done, for example, using an altimeter, user location information, information entered by the user, etc. In another embodiment, the impact the user has with an object (e.g., the impact of the user's feet with ground) is monitored. This may be done using an accelerometer or gyroscope. In some cases, the ambient temperature is measured. A group of reference activity types may be associated with bands of ambient temperature. For example, when the ambient temperature is zero degrees Celsius, activities such as skiing, sledding, and ice climbing are appropriate selections for reference activity types, whereas surfing, swimming, and beach volleyball may be inappropriate. The ambient humidity may also be measured (e.g., by a hygrometer). In some cases, pattern duration (i.e., the length of time for which particular movement pattern is sustained) is measured.

In one embodiment, monitoring the movement is accomplished using sensors configured to be attached to the user's body. Such sensors may include a gyroscope or accelerometer to detect movement, and a heart-rate sensor, each of which may be embedded in earphones that a user can wear, such as earphones 100. Additionally, various modules and sensors that may be used to perform the above-described operations may be embedded in electronic components of earphones 100 such as, for example, processor 165 and memory 175. In various embodiments, the above-described operations are performed by the movement monitoring module.

Method 1000, in one embodiment, involves determining the user activity type from the set of reference activity types. Once detected, the pattern may be used to determine the user activity type from the set of reference activity types. Each reference activity type is associated with a reference activity type pattern. The user activity type may be determined to be the reference activity type that has a reference activity type pattern that matches the pattern measured by method 1000.

In some cases, the pattern that matches the reference activity type pattern will not be an exact match, but will be substantially similar. In other cases, the patterns will not even be substantially similar, but it may be determined that the patterns match because they are the most similar of any patterns available. For example, the reference activity type may be determined such that the difference between the pattern of movement corresponding to the reference activity type and the pattern of movement is less than a predetermined threshold. In one embodiment, the pattern is looked up (for a match) in a reference activity type library. The reference activity type library may be included in metabolic table 1050. For example, the reference type library may include rows in a table such as the RAT rows 1058.

In further embodiments, method 1000 involves using the pattern frequency to determine the user activity type from the set of reference activity types. Several reference activity types may be associated with similar patterns (e.g., because the head moves in a similar pattern when running versus walking). In such cases, the pattern frequency may be used to determine the user activity type (e.g., because the pattern frequency for running is higher than the pattern frequency for walking).

Method 1000, in some instances, involves using additional information to determine the user activity type. For example, the pattern for walking may be similar to the pattern for running. The reference activity type of running may be associated with higher user velocities and the reference activity type of walking with lower user velocities. In this way, the velocity measured may be used to distinguish between two reference activity types having similar patterns.

In other embodiments, method 1000 involves monitoring the impact the user has with the ground and determining that, because the impact is larger, the activity type is running rather than walking, for example. If there is no impact, the user activity type may be determined to be cycling (or other activity type where there is no impact). In some cases, the humidity is measured to determine whether the user activity type is a water sport (i.e., whether the activity is being performed in the water). The reference activity types may be narrowed to those that are performed in the water, from which narrowed set of reference activity types the user activity type may be determined. In other cases, the temperature measured is used to determine the user activity type.

Method 1000 may entail instructing the user to confirm the user activity type. In one embodiment, a user interface is provided (e.g., using application 210) such that the user can confirm whether a displayed user activity type is correct or select the user activity type from a group of activity types.

In further embodiments, a statistical likelihood of choices for user activity type is determined. The possible user activity types are then provided to the user in such a sequence that the most likely user activity type is listed first (and then in descending order of likelihood). For example, it may be determined, based on the pattern, the pattern frequency, the temperature, and so on, that there is an 80% chance the user activity type is running, a 15% chance the user activity type is walking, and a 5% chance the user activity type is dancing. Via a user interface (e.g., using app 210), a list of these possible user activity types may be provided such that the user may select the user activity type the user is performing. In various embodiments, some of the above-described operations are performed by the metabolic loading module.

Figure 8C:
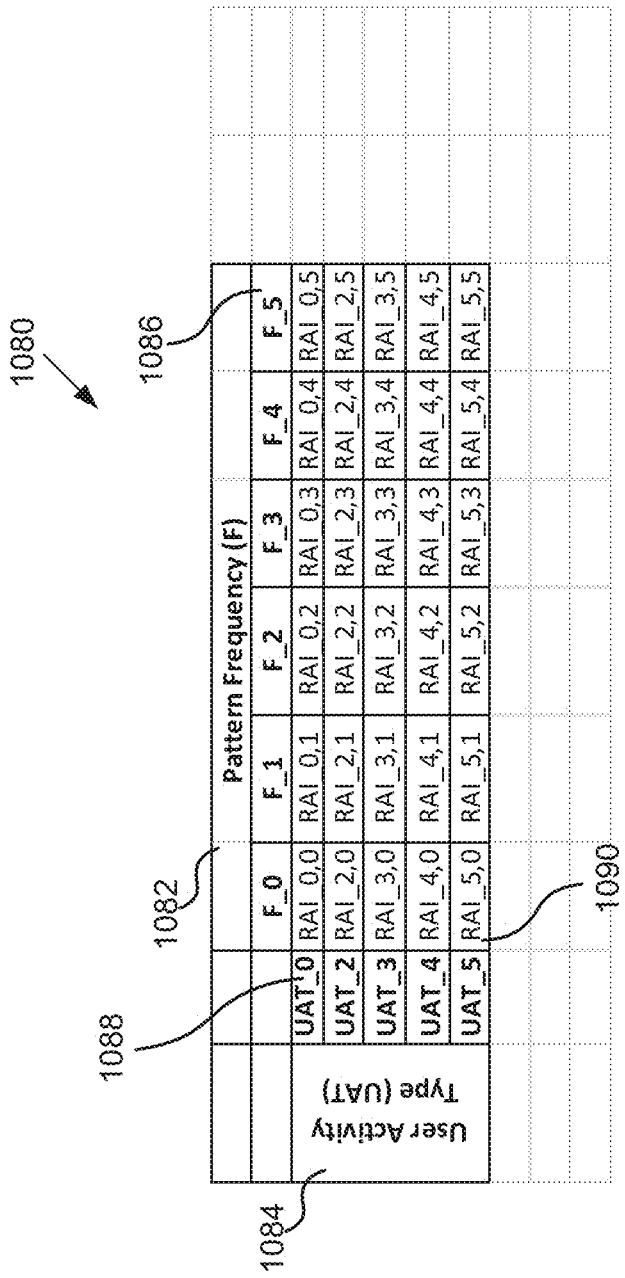
FIG. 8C is an example activity intensity library.

Method 1000, in some embodiments, also includes determining the user activity intensity from a set of reference activity intensities. The user activity intensity may be determined in a variety of ways. For example, the repetition period (or pattern frequency) and user activity type (UAT) may be associated with a reference activity intensity library to determine the user activity intensity that corresponds to a reference activity intensity. FIG. 8C illustrates one embodiment whereby this aspect of method 1000 is accomplished, including reference activity intensity library 1080. Reference activity intensity library 1080 is organized by rows 1088 of reference activity types 1084 and columns 1086 of pattern frequencies 1082. In FIG. 8C, reference activity library 1080 is implemented in a table. Reference activity library 1080 may, however, be implemented other ways.

In one embodiment, it is determined that, for user activity type 1084 UAT_0 performed at pattern frequency 1082 F_0, the reference activity intensity 1090 is RAI_0,0. UAT 1084 may, for example, correspond to the reference activity type for running, and a pattern frequency 1082 of 0.5 cycles per second for the user activity type may be determined. In addition, library 1080 may determine (e.g., at operation 1002) that the UAT 1084 of running at a pattern frequency 1082 of 0.5 cycles per second corresponds to an RAI 1090 of five on a scale of ten. In another embodiment, the reference activity intensity is independent of the activity type. For example, the repetition period may be five seconds, and this may correspond to an intensity level of two on a scale of ten regardless of the user activity type.

Reference activity intensity library 1080, in one embodiment, is included in metabolic table 1050. In some cases, the measured repetition period (or pattern frequency) does not correspond exactly to a repetition period for a reference activity intensity in metabolic table 1050. In such cases, the correspondence may be a best-match fit, or may be a fit within a tolerance defined by the user or by a system administrator, for example.

In various embodiments, method 1000 involves supplementing the measurement of pattern frequency to help determine the user activity intensity from the reference activity intensities. For example, if the user activity type is skiing, it may be difficult to determine the user activity intensity because the pattern frequency may be erratic or otherwise immeasurable. In such an example, the user velocity, the user's heart rate, and other indicators (e.g., breathing rate) may be monitored to determine how hard the user is working during the activity. For example, higher heart rate may indicate higher user activity intensity. In a further embodiment, the reference activity intensity is associated with a pattern speed (i.e., the speed or velocity at which a sensor is progressing through the pattern). A higher pattern speed may correspond to a higher user activity intensity.

Method 1000, in one embodiment, determines the user activity type and the user activity intensity using sensors attached to the user's body. Such sensors may include, for example, a gyroscope or accelerometer to detect movement, and a heart-rate sensor, each of which may be embedded in earphones that the user can wear on the user's head, such as earphones 100. Additionally, various sensors and modules that may be used to preform above-described operations of method 1000 may be embedded in earphones 100 and/or computing device 200. In various embodiments, the above-described operations are performed by the movement monitoring module.

Referring again to FIG. 8A, method 1000 includes creating and updating a metabolic activity score based on the movement and the user information. Method 1000 may also include determining a metabolic loading associated with the user and the movement. In one embodiment, a duration of the activity type at a particular activity intensity (e.g., in seconds, minutes, or hours) is determined. The metabolic activity score may be created and updated by, for example, multiplying the metabolic loading by the duration of the user activity type at a particular user activity intensity. If the user activity intensity changes, the new metabolic loading (associated with the new user activity intensity) may be multiplied by the duration of the user activity type at the new user activity intensity. In one embodiment, the activity score is represented as a numerical value. By way of example, the metabolic activity score may be updated by continually supplementing the metabolic activity score as new activities are undertaken by the user. In this way, the metabolic activity score continually increases as the user participates in more and more activities.

In one embodiment, the metabolic activity score is based on score periods. Monitoring the movement may include determining, during a score period, the metabolic loading associated with the movement. Score periods may include segments of time. The user activity type, user activity intensity, and the corresponding metabolic loading, in one embodiment, are measured (or determined) during each score period, and the metabolic activity score may be calculated for that score period. As the movement changes over time, the varying characteristics of the movement are captured by the score periods.

Method 1000 includes, in one embodiment, creating and updating a set of periodic activity scores. Each period activity score is based on the movement monitored during a set of score periods, and each period activity score is associated with a particular score period of the set of score periods. In one example, the metabolic activity score is created and updated as an aggregate of period activity scores, and the metabolic activity score may represent a running sum total of the period activity scores.

In one embodiment, method 1000 includes applying a score period multiplier to the score period to create an adjusted period activity score. The metabolic activity score in such an example is an aggregation of adjusted period activity scores. Score period multipliers may be associated with certain score periods, such that the certain score periods contribute more or less to the metabolic activity score than other score periods during which the same movement is monitored. For example, if the user is performing a sustained activity, a score period multiplier may be applied to the score periods that occur during the sustained activity. By contrast, a multiplier may not be applied to score periods that are part of intermittent, rather than sustained, activity. As a result of the score period multiplier, the user's sustained activity may contribute more to the metabolic activity score than the user's intermittent activity. The score period multiplier may allow consideration of the increased demand of sustained, continuous activity relative to intermittent activity.

The score period multiplier, in one instance, is directly proportional to the number of continuous score periods over which a type and intensity of the movement is maintained. The adjusted period activity score may be greater than or less than the period activity score, depending on the score period multiplier. For example, for intermittent activity, the score period multiplier may be less than 1.0, whereas for continuous, sustained activity, the score period multiplier may be greater than 1.0.

In one embodiment, method 1000 entails decreasing the metabolic activity score when the user consumes calories. For example, if the user goes running and generates a metabolic activity score of 1,000 as a result, but then the user consumes calories, the metabolic activity score may be decreased by 200 points, or any number of points. The decrease in the number of points may be proportional to the number of calories consumed. In other embodiments, information about specific aspects of the user's diet is obtained, and metabolic activity score points are awarded for healthy eating (e.g., fiber) and subtracted for unhealthy eating (e.g., excessive fat consumption).

The user, in one embodiment, is pushed to work harder, or not as hard, depending on the user lifestyle. This may be done, for example, by adjusting the metabolic loadings based on the user lifestyle. To illustrate, a user with a highly active lifestyle may be associated with metabolic loadings that result in a lower metabolic activity score when compared to a user with a less active lifestyle performing the same movements. This results in requiring the more active user to, for example, work (or perform movement) at a higher activity intensity or for a longer duration to achieve the same metabolic activity score as the less active user participating in the same activity type (or movements).

In one embodiment, the metabolic activity score is reset every twenty-four hours. The metabolic activity score may be continually incremented and decremented throughout a measuring period, but may be reset to a value (e.g., zero) at the end of twenty-four hours. The metabolic activity score may be reset after any given length of time (or measuring period)—for example, the activity score may be continually updated over the period of one week, or one month.

In one embodiment, because the metabolic activity score was greater than a certain amount for the measuring period, the metabolic activity score is reset to a number greater than zero. As such, the user effectively receives a credit for a particularly active day, allowing the user to be less active the next day without receiving a lower metabolic activity score for the next day. In a further embodiment, because the metabolic activity score was less than a predetermined value for the measuring period, the metabolic activity score is reset to a value less than zero. The user effectively receives a penalty for that day, and would have to make up for a particularly inactive or overly consumptive day by increasing the user's activity levels the next day. In various embodiments, creating and updating the metabolic activity score is performed by a movement monitoring module or by a metabolic activity score module.

Referring again to FIG. 8A, operation 1006 involves detecting a fatigue level. In one embodiment, the fatigue level is the fatigue level of the user. In one embodiment, the fatigue level is a function of recovery. In various embodiments, the fatigue level is described in terms of recovery. The fatigue level may be detected in various ways. In one example, the fatigue level is detected by calculating a heart rate variability (HRV) of the user using optical heartrate sensor 122 (discussed above in reference to FIG. 2B). Further, possible representations of the fatigue level are described above (e.g., numerical, descriptive, etc.). When the HRV is more consistent (i.e., steady, consistent amount of time between heartbeats), for example, the fatigue level may be higher. In other words, with a higher fatigue level, the body is typically less fresh and less well-rested. When HRV is more sporadic (i.e., amount of time between heartbeats varies largely), the fatigue level may be lower.

At operation 1006, HRV may be measured in a number of ways (e.g., as discussed above in reference to FIGS. 2B and 3A-3C). Measuring HRV, in one embodiment, involves optical heartrate sensor 122 measuring changes in blood flow. Light reflected back through the skin of the user's ear may be obtained with a receiver (e.g., a photodiode) and used to determine changes in the user's blood flow, thereby permitting calculation of the user's heart rate using algorithms known in the art. Using the data collected by sensor 122, processor 165 may calculate the HRV based on a time domain methods, frequency domain methods, and other methods known in the art that calculate HRV based on data such as the mean heart rate, the change in pulse rate over a time interval, and other data used in the art to estimate HRV. In other embodiments, HRV may be measured using electrocardiography (ECG) or photoplethysmography (PPG) sensors mounted on other parts of the user's body, such as, for example, sensors mounted on the wrist, finger, ankle, leg, arm, or chest.

In one embodiment, at operation 1006, the fatigue level is detected based solely on the determined HRV. The fatigue level, however, may be based on other measurements (e.g., measurements monitored by method 1000). For example, the fatigue level may be based on the amount of sleep that is measured for the previous night, the user activity duration, the user activity type, and the user activity intensity determined for a previous time period (e.g., exercise activity level in the last twenty-four hours). By way of example, these factors may include stress-related activities such as work and driving in traffic, which may generally cause a user to become fatigued. In some cases, the fatigue level is detected by comparing the HRV measured to a reference HRV. This reference HRV may be based on information gathered from a large number of people from the general public. In another embodiment, the reference HRV is based on past measurements of the user's HRV.

At operation 1006, in one embodiment, the fatigue level is detected once every twenty-four hours. This provides information about the user's fatigue level each day so that the user's activity levels may be directed according to the fatigue level. In various embodiments, the fatigue level is detected more or less often. Using the fatigue level, the user may determine (a) whether or not an activity is necessary (or desirable), (b) the appropriate user activity intensity, and (c) the appropriate user activity duration. For example, in deciding whether to go on a run, or how long to run, the user may want to use operation 1006 to assess the user's current fatigue level. Then, the user may, for example, run for a shorter time if the user is more fatigued, or for a longer time if the user is less fatigued. In some cases, it may be beneficial to detect the fatigue level in the morning when the user wakes up. This may provide the user a reference for how the day's activities should proceed.

Referring again to FIG. 8A, operation 1008 involves creating and updating a dynamic recovery profile based on an archive. The archive includes historical information about the fatigue level (which is described above with reference to operation 1006). In one embodiment, the archive includes historical information about the movement and the metabolic activity score. The archive may include, for example, information about past user activity types, past user activity intensities, and past fatigue levels, as well as the relationships between each of these (e.g., if fatigue levels are particularly high after a certain user activity type or after a user achieves a particular metabolic activity score). The archive may also include historical information relative to particular score periods and score period multipliers. The archive, in various embodiment, is stored in apparatus 702 (e.g., computing device 200) or computing device 708 (e.g., earphones 100).

The dynamic recovery profile is created and updated based on the archive. In one embodiment, being based on the user's actual (historical) and detected fatigue level, the dynamic recovery profile is specific to the user's personal fatigue characteristics and responses. The dynamic recovery profile, for example, may reflect information indicating that the user typically has a very high fatigue level when the user gets less than six hours of sleep. In another instance, the dynamic recovery profile may indicate that the user typically has a very high fatigue level following a day in which the user achieves a metabolic activity score above a certain amount (or a particular user activity intensity that is sustained over a particular amount of time). In another example, the user's fatigue levels may not follow typical trends, and the archive can account for this. For example, while the average user may present a fatigue level of 4 when well rested, the archive may reflect that the user has recorded a fatigue level of 6 when rested. The archive provides a means for the fatigue level measurement to be normalized to the user's specific HRV and fatigue levels.

The dynamic recovery profile, in other words, learns the fatigue tendencies of the user by compiling, by way of the archive, data about the user. Moreover, the dynamic recovery profile provides a contoured baseline that is continually adjusted as the user's performance, fatigue, and recovery tendencies change over time. In one embodiment, the dynamic recovery profile represents a range of fatigue levels that are normal for the user. For example, based on data in the archive, the dynamic recovery profile may indicate that fatigue levels between 40 and 60 are typical for the user. The dynamic recovery profile, in one embodiment, accounts for changes in the historical information over time by updating the dynamic recovery profile on a periodic basis. In a further embodiment, the user programs the dynamic recovery profile to refresh periodically to capture recent historical information. Updates to the dynamic recovery profile, in one instance, are based on rates or amounts of change that may occur over time to the historical information in the archive.

Figure 8D:
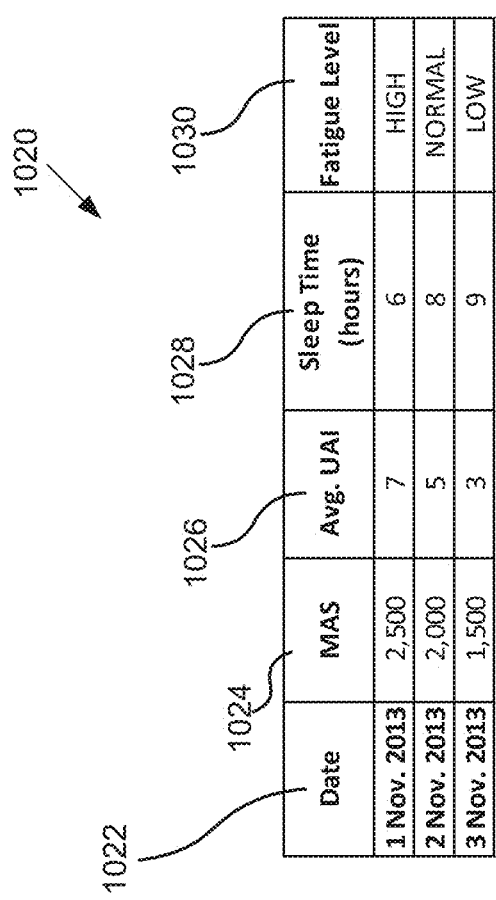
FIG. 8D is an example of an archive table.

The dynamic recovery profile, in one embodiment, is implemented in conjunction with an archive table that represents data and relationships of parameters relative to that data. In one instance, the archive table uses the parameters of metabolic activity score (MAS), date, fatigue level, sleep time, and average user activity intensity (UAI) to organize the data and extract relational information. This is illustrated in FIG. 8D, which provides archive table 1020 (which may be embodied in the archive). Archive table 1020 includes the parameters of date 1022, MAS 1024, average UAI 1026, sleep time 1028, and fatigue level 1030. In other instances, archive table 1020 may include only information about the user's measured fatigue levels.

In various embodiments, archive table 1020 includes any other parameters that are monitored, determined, or created by method 1000. In some embodiments, archive table 1020 includes analytics. Such analytics include statistical relationships of the various parameters in archive table 1020. For example, archive 1020 may include analytics such as mean ratio of fatigue level to MAS, mean ratio of sleep to MAS, mean fatigue level by day of the week, and so on. These analytics allow the dynamic recovery profile to back into optimal performance regimens specific to the user.

To illustrate, the dynamic recovery profile may determine (from archive table 1020) that the user has a mean fatigue level of 7 following a day when sleep to MAS ratio is 6 to 2,000, and may determine that the user typically achieves a below average MAS on days when the fatigue level is 7 or higher. In such an example, the dynamic recovery profile may indicate that the user should get more sleep, or should strive for a lower MAS, to avoid becoming overly fatigued. The dynamic recovery profile, in one embodiment, reflects information about the user's optimal fatigue scenarios; that is, fatigue levels at which the user tends to historically achieve a high MAS. The optimal fatigue scenario may be specific to the user (e.g., some users may have greater capacity for activity when more fatigued, etc.).

Referring again to FIG. 8A, operation 1010 involves creating and updating an interpreted recovery score based on the fatigue level and the dynamic recovery profile. The interpreted recovery score, because it is based on both the fatigue level detected and on actual, historical results (as incorporated into the dynamic recovery profile), provides higher resolution and additional perspective into the user's current performance state. In one embodiment, the interpreted recovery score supplements the fatigue level with information to account for the user's past activities (e.g., from the archive). The interpreted recovery score may be, for example, a number selected from a range of numbers. In one case, the interpreted recovery score may be proportional to the fatigue level (e.g., higher fatigue corresponds to higher interpreted recovery score). In one embodiment, a typical interpreted recovery score ranges from 40 to 60.

The interpreted recovery score, by way of the dynamic recovery profile (which is based on the archive), in one embodiment, has available information about the user activity type, the user activity intensity, and the duration of the user's recent activities, as well as analytics of historical information pertaining to the user's activities. The interpreted recovery score may use this information, in addition to the current fatigue level, to provide higher resolution into the user's capacity for activity. For example, if the user slept poorly, but for some reason this lack of sleep is not captured in the fatigue level measurement (e.g., if the HRV is consistent rather than sporadic), the interpreted recovery score may be adjusted to account for the user's lack of sleep. In this example, the lack of sleep information would be available via archived activity type detection and movement monitoring. In other embodiments, the interpreted recovery score will be based only on historic fatigue levels specific to the user. In various embodiments, operation 1010 is performed by interpreted recovery score module 808.

Figure 9:
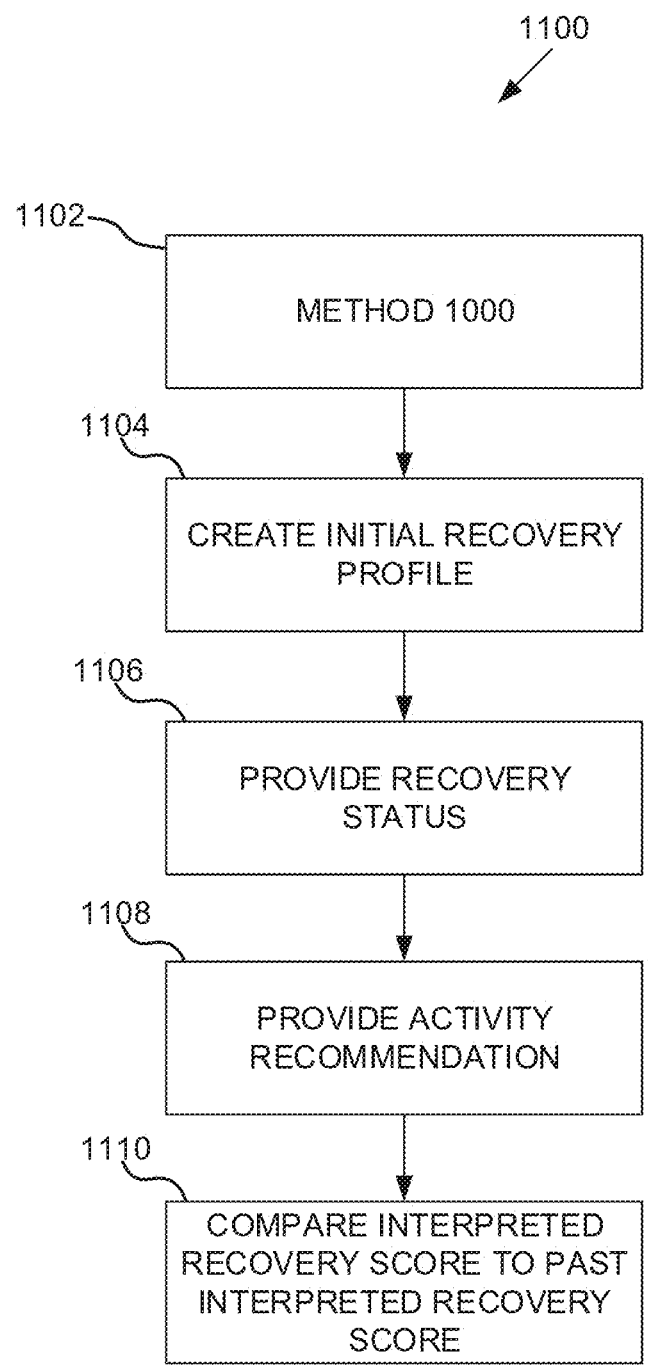
FIG. 9 is an operational flow diagram illustrating an example of a method for providing an interpreted recovery score including providing a recovery status.

FIG. 9 is an operational flow diagram illustrating an example method 1100 for providing an interpreted recovery score in accordance with an embodiment of the present disclosure. In one embodiment, apparatus 702 (e.g., computing device 200) and earphones 100 perform various operations of method 1100. In addition, method 1100 may include, at operation 1102, various operations from method 1000.

At operation 1104, an initial recovery profile is created. The initial recovery profile is based on a comparison of the user information to normative group information. The normative group may include information collected from a group of people other than the user. The normative group information may be averaged and used as a baseline for the initial recovery profile (an expectation of user activity levels) before any historical information is generated.

The normative group information, in one embodiment, is adjusted according to different possible sets of user information. For example, the normative group information may be collected and averaged (or otherwise statistically analyzed). A user information multiplier may be created based on a comparison of the normative group information and the user information. The user information multiplier may be applied to the normative group information to adjust the normative group information such that the normative group information becomes specific to the user's information and characteristics. For example, an average value of the normative group information may be increased if the user is younger than the average group member, or may decrease the average for a user that is less active than the average group member. This adjustment, in one embodiment, results in an initial recovery profile that is based on the normative group information but is specific to the user information (and the user). The initial recovery profile may represent a user-specific expectation for activity level (e.g., for MAS). The initial recovery profile may also represent a user-specific expectation for fatigue level. In various embodiments, operation 1104 is performed by initial recovery profile module 902.

In one embodiment, creating and updating the dynamic recovery profile is further based on the initial recovery profile. In such an embodiment, if the historical information about the user's fatigue levels indicates that the user is typically more fatigued than the user's initial recovery profile indicates the user is expected to be, the dynamic recovery profile is updated in a way that reflects this discrepancy. For example, based on actual fatigue levels detected, the dynamic recovery profile may expect a higher fatigue level than indicated by the initial recovery profile.

The dynamic recovery profile, in one embodiment, learns over time what fatigue levels or range of fatigue level is normal from the user. During this learning phase, the dynamic recovery profile may include a blend of information from the archive and the initial recovery profile. The dynamic recovery profile, in such an embodiment, more heavily weighs the information from the archive as the archive gathers information that is increasingly complete. For example, before taking any fatigue measurements, the dynamic recovery profile may be based entirely on the initial recovery profile (which is derived from normative data).

Then, for example, after detecting and storing in the archive two weeks' worth of fatigue level information from the user the dynamic recovery profile may weigh the information from the archive more heavily (e.g., base the dynamic recovery profile 50% on the archive and 50% on the initial recovery profile). Eventually, once the dynamic recovery profile captures complete information in the archive (e.g., after two months' worth of detecting fatigue level information), the dynamic recovery profile may phase out the initial recovery profile entirely. That is, the dynamic recovery profile may be entirely based on the archive. In other words, the dynamic recovery profile, in such an embodiment, phases out the initial recovery profile as the amount of information in the archive increases.

In further embodiments, the historical information about the user activity type or user activity intensity (or MAS) may differ from the initial recovery profile in a way that warrants a shift in expected activity levels. For example, the initial recovery profile may expect a higher or lower amount of user activity intensity (or MAS) than is in reality measured. This discrepancy may be resolved by updating the dynamic recovery profile based on the archive. For example, the dynamic recovery profile may be decreased because the user is not performing at the level (e.g., MAS) initially expected (or indicated by the initial recovery profile).

In addition, the user information may change in a way that causes the initial recovery profile, created at operation 1104, to lose its accuracy. The dynamic recovery profile may be updated to reflect such changes, such that the dynamic recovery profile is more accurate. For example, the user's weight or age may change. As a result, the normative group data used to generate the initial recovery profile may become stale. This may be resolved by updating the dynamic recovery profile (e.g., with the user's actual weight). The dynamic recovery profile may function as a version of the initial recovery profile adjusted according to the historical information in the archive.

Referring again to FIG. 9, at operation 1106 a recovery status is provided based on the interpreted recovery score. The recovery status may be based on various thresholds of the interpreted recovery score. For example, the recovery status may be represented on a numerical, descriptive, or color scale, or the like. In one instance, the recovery status is directly proportional to the interpreted recovery score. The recovery status, in such an example, may indicate the user's need to rest from strenuous activity or high levels of activity. In the case that the recovery status is numerical, a negative recovery status may indicate that the user is over-rested, a positive recovery status may indicate that rest is needed, and a small recovery status (i.e., near-zero) may indicate an optimal recovery level.

In one embodiment of the descriptive recovery status, the recovery status includes the following: fatigued, recovered, and optimal. If the interpreted recovery score is below a lowest threshold, in the descriptive recovery status example, the recovery status will be "recovered." This indicates that the user is fully rested. In some instances, "recovered" is distinguished from "optimal" because "recovered" indicates that the user is too rested and has less capacity for activity. Further illustrating the descriptive recovery status example, if the interpreted recovery score is above the lowest threshold but below the highest threshold, the recovery status will be "optimal." This indicates that the user has peak capacity for activity. "Optimal" recovery status may be associated with the scenario in which the user is rested, but no overly so. If the interpreted recovery score is above the highest threshold, the recovery status (in this example) will be "fatigued." This indicates that the user has minimal capacity for activity because the user needs to rest. In various embodiments, the recovery status is based on any number of thresholds and may be further stratified for higher granularity into the user's recovery status.

At operation 1108, an activity recommendation is provided based on the interpreted recovery score. For example, if the interpreted recovery score is high, indicating that the user is more fatigued, lower user activity intensities may be recommended. If the interpreted recovery score is low, indicating that the user is well-rested, higher activity intensities may be recommended. This example applies to recommended activity durations in a similar fashion (e.g., longer durations if less fatigued, etc.).

At operation 1110, the interpreted recovery score is compared to a past interpreted recovery score. In this embodiment, the interpreted recovery score is associated with a measuring period and the past interpreted recovery score is associated with a past measuring period. Interpreted recovery scores may be stored and associated with past measuring periods (i.e., the measured period during which the interpreted recovery score was created). In this way, past interpreted recovery scores and information associated therewith may be used to inform the user's current activity.

In embodiments, comparing the scores may include providing a simple numerical readout of both scores (e.g., side by side). In one embodiment, information about the time of day associated with the past interpreted recovery score is presented. For example, the time of day at which the past interpreted recovery score was created may be presented. This may inform the user of how the user's current interpreted activity score relates to the past interpreted recovery score, allowing the user to gauge how the interpreted recovery score may correlate to the user's physical state or feeling.

In another embodiment, the past interpreted recovery score is displayed on a graph (e.g., a line or bar graph) as a function of time (e.g., comparing against other past interpreted recovery scores from past measuring periods). The graph may be overlaid with a graph of the current interpreted recovery score. One of ordinary skill in the art will appreciate other ways to compare the interpreted recovery scores. In various embodiments, operation 1110 is performed by interpreted recovery score module 808.

Figure 10:
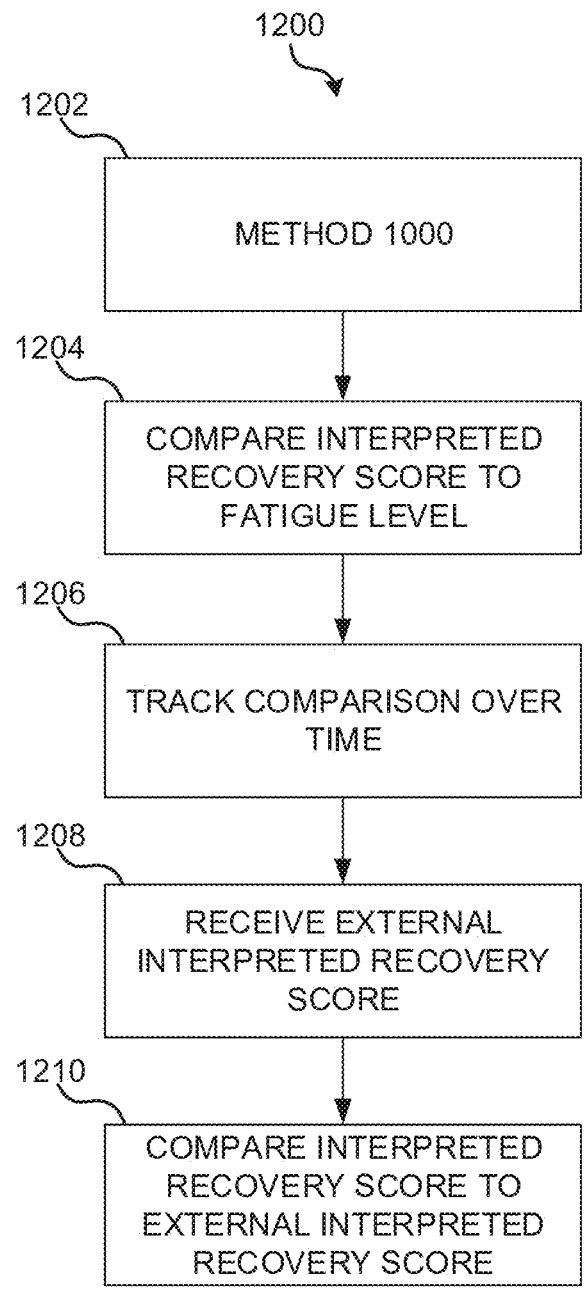
FIG. 10 is an operational flow diagram illustrating an example of a method for providing an interpreted recovery score including comparing the interpreted recovery score to an external interpreted recovery score.

FIG. 10 is an operational flow diagram illustrating an example method 1200 for providing an interpreted recovery score in accordance with an embodiment of the present disclosure. In one embodiment, apparatus 702 (e.g., computing device 200) and earphones 100 perform various operations of method 1200.

At operation 1204, the interpreted recovery score is compared with the fatigue level. At operation 1206, the comparison is tracked over time. As described above, the fatigue level may be associated with physical phenomena, including HRV, while the interpreted recovery score is based on actual, historical information (via the dynamic recovery profile), include past fatigue levels for the user. In one embodiment, tracking the comparison over time (operation 1206) provides insight into how lifestyle choices affect performance capacity and fatigue levels. For example, the comparison may provide a normalization for the user's typical fatigue levels as they change over time relative to past fatigue levels.

At operation 1208 an external interpreted recovery score is received. The external interpreted recovery score may be received in a number of ways (e.g., via communication medium 704). The external interpreted recovery score may be created and updated in a manner similar to the creating and updating of the interpreted recovery score (operation 1010). The external interpreted recovery score may be received from a second user. The second user may be a friend or associate of the first user. In various embodiments, operation 1208 is performed by interpreted recovery score module 808.

At operation 1210, the external interpreted recovery score is compared to the interpreted recovery score. The external interpreted recovery score may be compared to the interpreted recovery score in a fashion substantially similar to the comparison performed in operation 1110. Operation 1210 allows the user to compare the user's interpreted recovery score (based on the user's fatigue level) to the interpreted recovery score of another user (based on the other user's fatigue level). In various embodiments, operation 1210 is performed by interpreted recovery score module 808.

Referring back to method 1000 one or more operations may be further leveraged to provide additional information to a user. For example, various embodiments of the present disclosure may identify when a user is progressing through a "fitness cycle." As utilized herein, the term fitness cycle may refer to a period that spans experiencing some type of physical load, e.g., a workout, through recovery. That is, HRV can be determined and leveraged (in the context of learned user characteristics/recovery profile described above) in such a way as to identify and present fitness cycle information to a user.

Figure 11A:
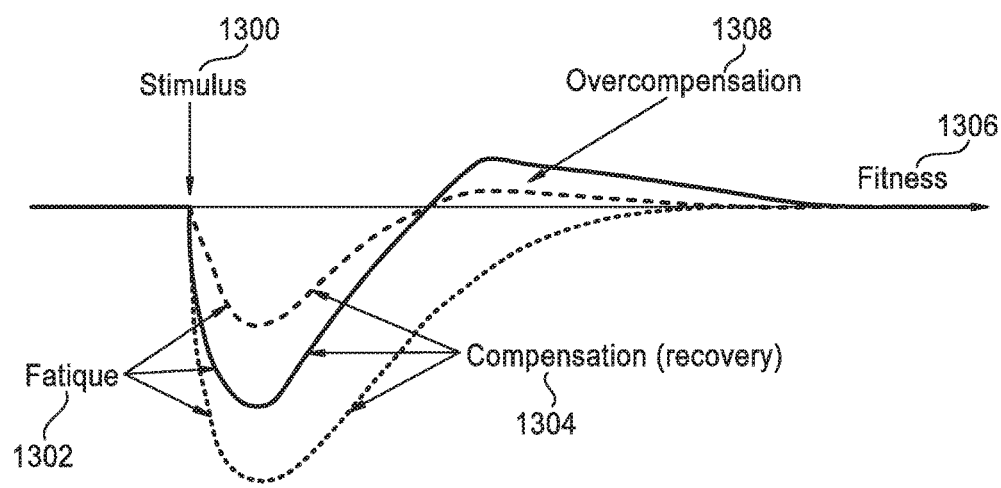
FIG. 11A is an example graphical representation of fitness cycles.
Figure 11B:
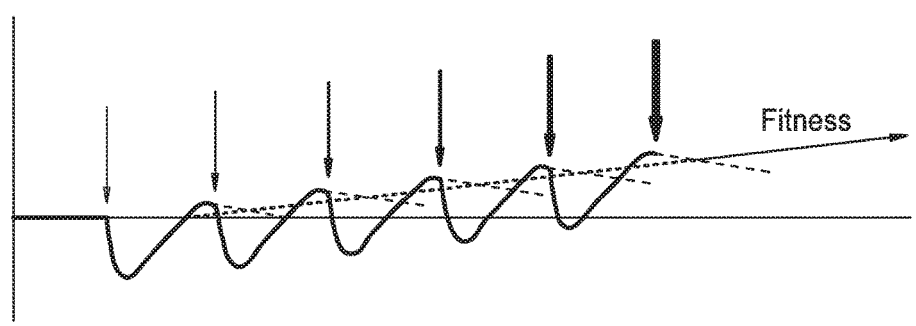
FIG. 11B is an example graphical representation of a plurality of fitness cycles over time.

That is, fitness gains are generally made when the human body fully recovers from an activity, such as a workout. FIGS. 11A and 11B are graphs representing example fitness cycle information/data that may be obtained and/or presented to a user in accordance with one embodiment. In particular, FIG. 11A illustrates example fitness cycles. A stimulus or load 1300 may be experienced by the human body during a workout, where the fitness level of the human body, i.e. the ability to perform work at a given rate, decreases as the workout progresses. In other words, the human body becomes fatigued. Different levels of fatigue 1302 can be experienced depending whether, e.g., a training session was adequate (solid line), too easy (hashed line), or too hard (dotted line). After the end of the workout, which would correspond with the greatest level of fatigue experienced, the human body can begin to rebuild itself (e.g., rebuild muscle fibers and nervous system) to return to its original baseline fitness level 1306. The period from this state of post-workout fatigue back to the original baseline fitness level 1306 may be referred to as compensation or recovery 1304. It should be noted that recovery can be considered a function of fatigue (or vice-versa), where for example, as the human body becomes less fatigued, from, e.g., rest, the human body can be considered to be undergoing recovery.

If the human body is allowed to properly recover between an initial instance of fatigue and a subsequent activity, such as another workout, the human body can experience a phenomenon referred to as overcompensation 1308, which can be a continuation of the recovery process. Overcompensation can occur when the human body (e.g., muscle fibers and nervous system) is built up beyond the original baseline fitness level 1306, creating a new fitness level that surpasses the original baseline fitness level.

FIG. 11A illustrates an example graphical representation of fitness level 1306 over time. If overcompensation occurs subsequent to each workout, over time, the human body can experience increased baseline fitness levels 1306 and/or can increased capability for athletic performance.

However, if the human body engages in stimuli or loading, such as subsequent workouts, before proper recovery can occur, or if the resulting fatigue level is too severe, overcompensation can fail to occur, and athletic performance and fitness may either remain stagnant or, in some instances, may even degrade. Additionally still, workouts that are too easy and/or engaging in recovery that lasts too long may also result in static fitness levels. Accordingly, a user presented with information regarding when the user is progressing through fitness cycles can determine whether or not they are engaging in activity and recovery that is improving their fitness in a quantifiable manner, and thereby allowing for adjustment(s) to their activity and recovery. It should be noted that stress (as previously discussed) may be considered to be a stimulus from which fatigue can result.

Figure 12:
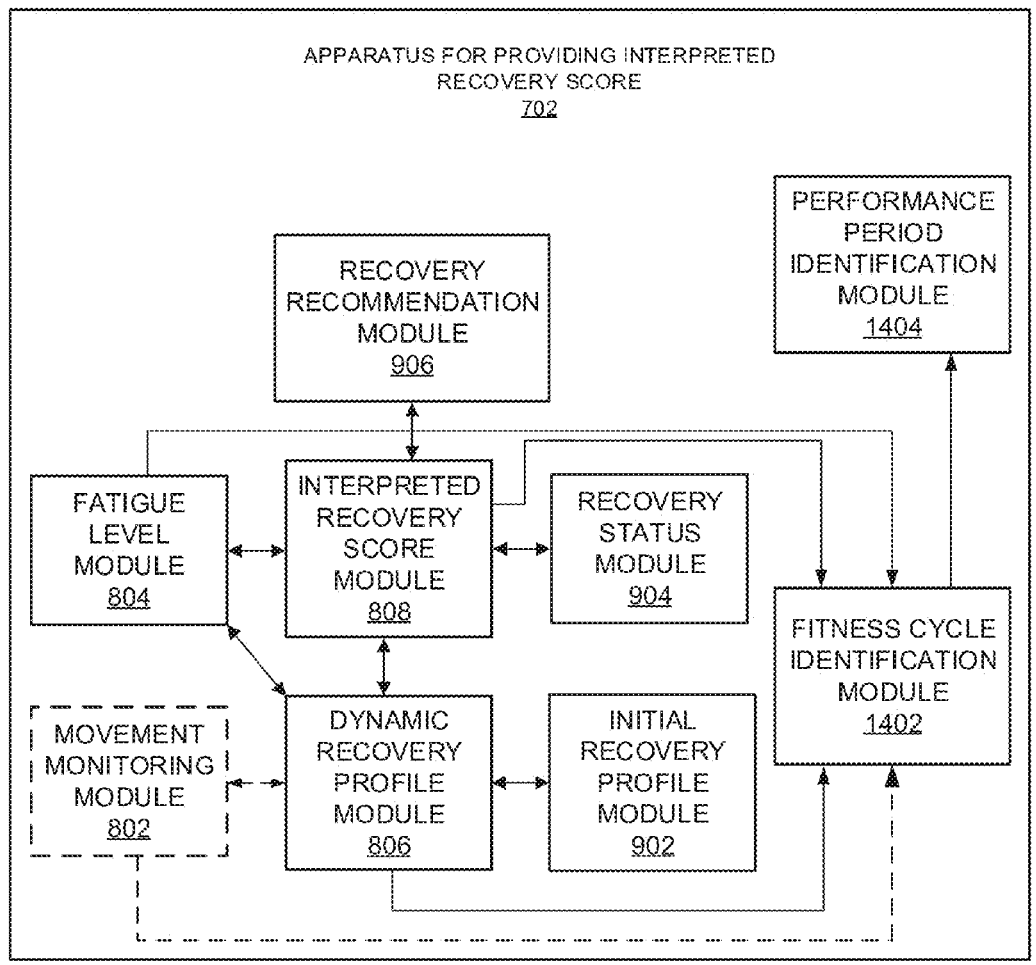
FIG. 12 illustrates the example apparatus for providing an interpreted recovery score of FIG. 7 utilized as a platform for identifying performance periods.

FIG. 12 is a schematic block diagram illustrating one embodiment of an apparatus for providing an interpreted recovery score 702 being utilized as a platform for identifying performance periods. Apparatus 702 may include movement monitoring module 802 (which can be optional as described above), fatigue level module 804, dynamic recovery profile module 806, and interpreted recovery score module 808, each of which have been described previously. Apparatus 702 may also include initial recovery profile module 902, recovery status module 904, and recovery recommendation module 906, each of which have also been previously described. Additionally, apparatus 702 may further include fitness cycle identification module 1402, and performance period identification module 1404, each of which will be described below in further detail with regard to various processes.

In one embodiment, at least one of movement monitoring module 802, fatigue level module 804, dynamic recovery profile module 806, interpreted recovery score module 808, initial recovery profile module 902, recovery status module 904, recovery recommendation module 906, fitness cycle identification module 1402, and performance period identification module 1404 are embodied in a wearable device such as earphones 100. In various embodiments, any of the modules described herein may be embodied in earphones 100, and may connect to other modules described herein via communication medium 704. In additional embodiments, any of the modules described herein may be embodied in computing device 200. In other embodiments, any of the modules described herein may be embodied in other sensors or devices, e.g., chest heart rate monitor, wristband, armband, etc.

Figure 13:
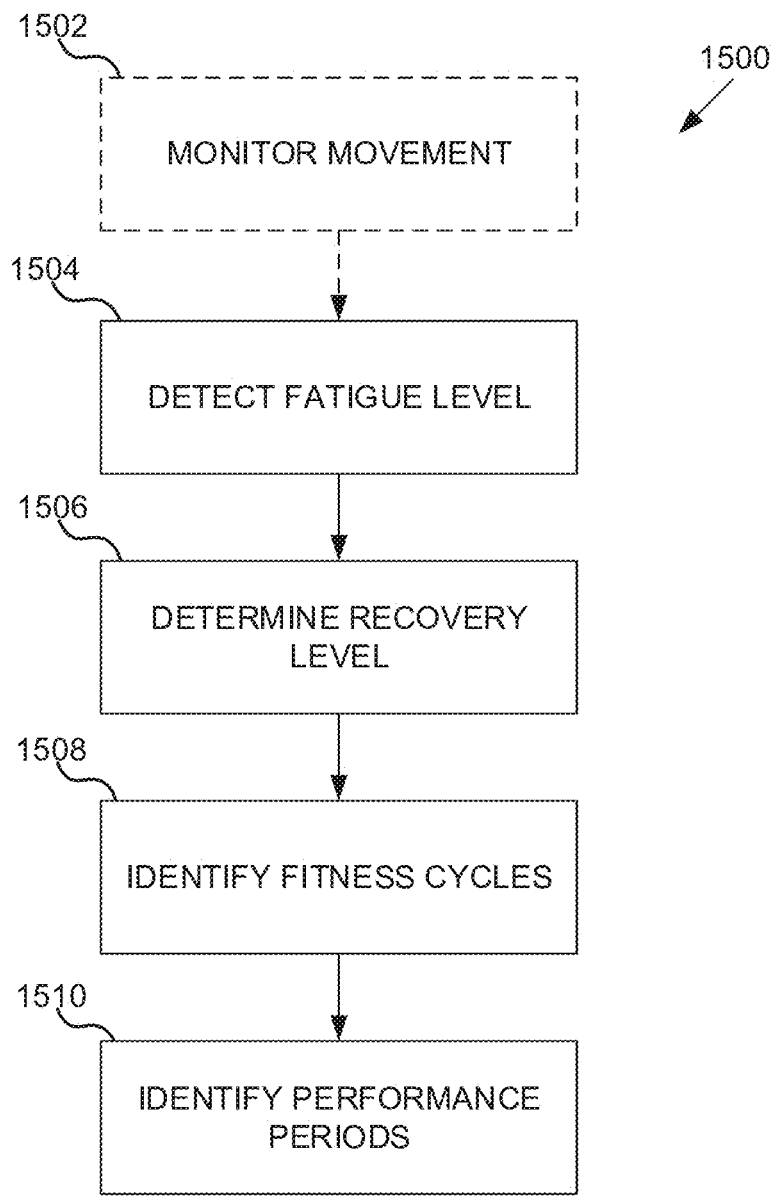
FIG. 13 is an operational flow diagram illustrating an example method for identifying performance periods.

FIG. 13 is an operational flow diagram illustrating an example method 1500 for identifying performance periods in accordance with an embodiment of the present disclosure. The operations of method 1500 can utilize information, such as detected fatigue level and, in one embodiment, a user's actual (historical) fatigue, e.g., from learned user characteristics that can be or can include, e.g., a fatigue profile, such as described above, in order to identify fitness cycles and/or present information or data associated with fitness cycles. As a result of identifying fitness cycles, optimal performance periods may also be identified/predicted.

At operation 1504 (similar to operation 1006 described above), fatigue level may be detected. The fatigue level may be detected in various ways. In one example, the fatigue level is detected by calculating the HRV of a user using optical heart rate sensor 122 as described above. In various embodiments, the fatigue level may be detected more or less frequently, and in accordance with one embodiment, may be detected periodically subsequent to each time some type of stimulus or load indicative of, e.g., some form of exercise or other fitness-related activity, is detected or otherwise determined to have occurred.

In one embodiment, at an optional operation 1502, movement can be monitored in order to identify and/or characterize a stimulus or load placed on the human body of the user, indicating the beginning of a fitness cycle. Optional operation 1502 can monitor movement based on the aforementioned RAT, monitoring movement patterns, intensity, etc. to determine if the movement is indicative of a stimulus associated with, e.g., some fitness-related activity. In embodiments, the movement may be monitored using motion sensor 121 of earphones 100.

At operation 1506, a recovery level may be determined. The recovery level can be determined, as described above, from one or more of determining a dynamic recovery profile (similar to operation 1008 described above), and determining an interpreted recovery score (similar to operation 1010 described above).

At operation 1508, fitness cycles can be identified based upon periods of activity through recovery, as determined through detection of fatigue level, and recovery level (as well as any movement monitoring) described above, where operation 1508 may be performed by fitness cycle identification module 1402. Accordingly, based on a user's measured HRV and history, the user's fatigue level and recovery level can be determined and presented to a user to characterize a fitness cycle progressed through by the user. The presentation of such data may be in a variety of forms, whether numerically, descriptively, or visually, such as in a graph or timeline format.

As alluded to previously, providing the user with the awareness of when he or she is moving or has moved through a fitness cycle may allow the user to improve fitness and athletic ability. That is, by training or engaging in activities that provide an optimum fatigue level and waiting for proper recovery before subsequent training or engagement in additional activities, overcompensation can occur. Further still, the user can be made aware of his or her athletic or fitness progression by presenting aggregated information or data regarding a plurality of fitness cycles, such as sets of fitness cycles that may be, e.g., contiguous or non-contiguous in time.

It should be noted that in accordance with other embodiments, the detection of fatigue, as well as movement monitoring (when optionally utilized), may be tailored or focused on a particular type of activity, sets of activity, etc. For example, a user may wish to identify fitness cycles relevant to cycling activities rather than weight-lifting activities. Alternatively, the user may wish to gather and/or aggregate data regarding sets of one or more activities associated with a workout session, for example. In one embodiment, fitness cycle identification module 1402 may aggregate various stimuli detected by optional movement monitoring module 802 (and associated with a workout session), determine an aggregate fatigue level resulting from the various stimuli, and identify and/or present fitness cycles commensurate with the workout session and resulting recovery.

It should be further noted that presentation of fitness cycle information can be accomplished in variety of ways. For example, fitness cycle information can be presented in a visual/graphical manner, similar to that illustrated in FIGS. 11A-11B Alternatively or in addition to such visual representations, fitness cycles information can be quantified and/or otherwise described and presented to a user in a textual, numerical, or descriptive manner.

At operation 1510, performance periods may be identified or predicted, where operation 1510 may be performed by performance period identification module 1404. For example, and depending upon when a fitness cycle has been identified or occurs, an optimal performance period may be predicted by determining periods residing within fitness cycles.

As described above, HRV or HRV in combination with metrics, can be used to calculate a fatigue level. For example, earphones 100 and computing device 200 may detect the amount of physical activity and the amount of sleep a user experienced over the last 48 hours, combine those metrics with the user's calculated HRV, and calculate a fatigue level of between 1 and 10, wherein the fatigue level could indicate the user's physical condition and aptitude for further physical activity that day. The fatigue level may also be calculated on a scale of between 1 and 100, or any other scale or range. In one embodiment, the typical fatigue level ranges from about 40 to 60. The fatigue level may also be represented on a descriptive scale; for example, low, normal, and high.

Additionally, as also described above, an interpreted recovery score, because it is based on both the fatigue level detected and on actual, historical results (as incorporated into the dynamic recovery profile), provides higher resolution and additional perspective into the user's current performance state. In one embodiment, the interpreted recovery score supplements the fatigue level with information to account for the user's past activities from the archive (i.e. learned user characteristics). The interpreted recovery score may be selected from a range of numbers, and again, in one case, the interpreted recovery score may be proportional to the fatigue level, where a typical interpreted recovery score ranges from 40 to 60.

Depending on how performance periods may be designated or defined (which can be configured, e.g., at some default designation(s), value(s), range(s), or tailored to a particular user(s)), a performance period may be associated with a particular fatigue level. For example, a fatigue level between the range of 40 to 60 may be considered to be a period of recovery, which can be correlated to or interpreted/identified as a performance period. That is, a fatigue level of 30 may be indicative that a user is still too fatigued, while a fatigue level in the range of 60 to 80 may be indicative that the user is fresh/fully recovered. Accordingly, performance periods, in one embodiment, can be regarded as periods of optimal performance/activity that can result in a trend of proper overcompensation, which over time can result in increased fitness levels.

Periods of optimal performance, as determined or predicted at operation 1510 may be presented or identified to a user in at least one of a numerical, descriptive, or visual manner (e.g., using application 210). Moreover, the presentation or identification of such periods of optimal performance can be performed separately from or commensurate with the presentation of data associated with or characterizing the fitness cycles described above. For example, and in accordance with one embodiment, when a plurality of fitness cycles are illustrated to the user in a graphical format (e.g., fitness level as a function of time), visual indicators may be placed within illustrated fitness cycles to indicate optimal performance periods.

In one embodiment, the operations of method 1000, method 1100, method 1200, and method 1500 are performed using sensors configured to be attached to the user's body. Such sensors may include a gyroscope or accelerometer to detect movement, and a heart-rate sensor, each of which may be embedded in earphones that a user can wear on the user's ears such as earphones 100. Such sensors may be used in conjunction with processors and memories/storages to perform the operations of monitoring the movement, detecting the fatigue level, creating and updating the dynamic recovery profile, and creating and updating the interpreted recovery score, or any other operation disclosed herein. In further embodiments, sensors used to perform these operations may be standalone sensors, and may not attach to the body.

FIGS. 14-17 illustrate a particular implementation of a GUI for activity tracking application 210 comprising displays associated with each of display modules 211-214. In various embodiments, the GUI of activity tracking application 210 may be used to identify performance periods for the user.

Figure 14:
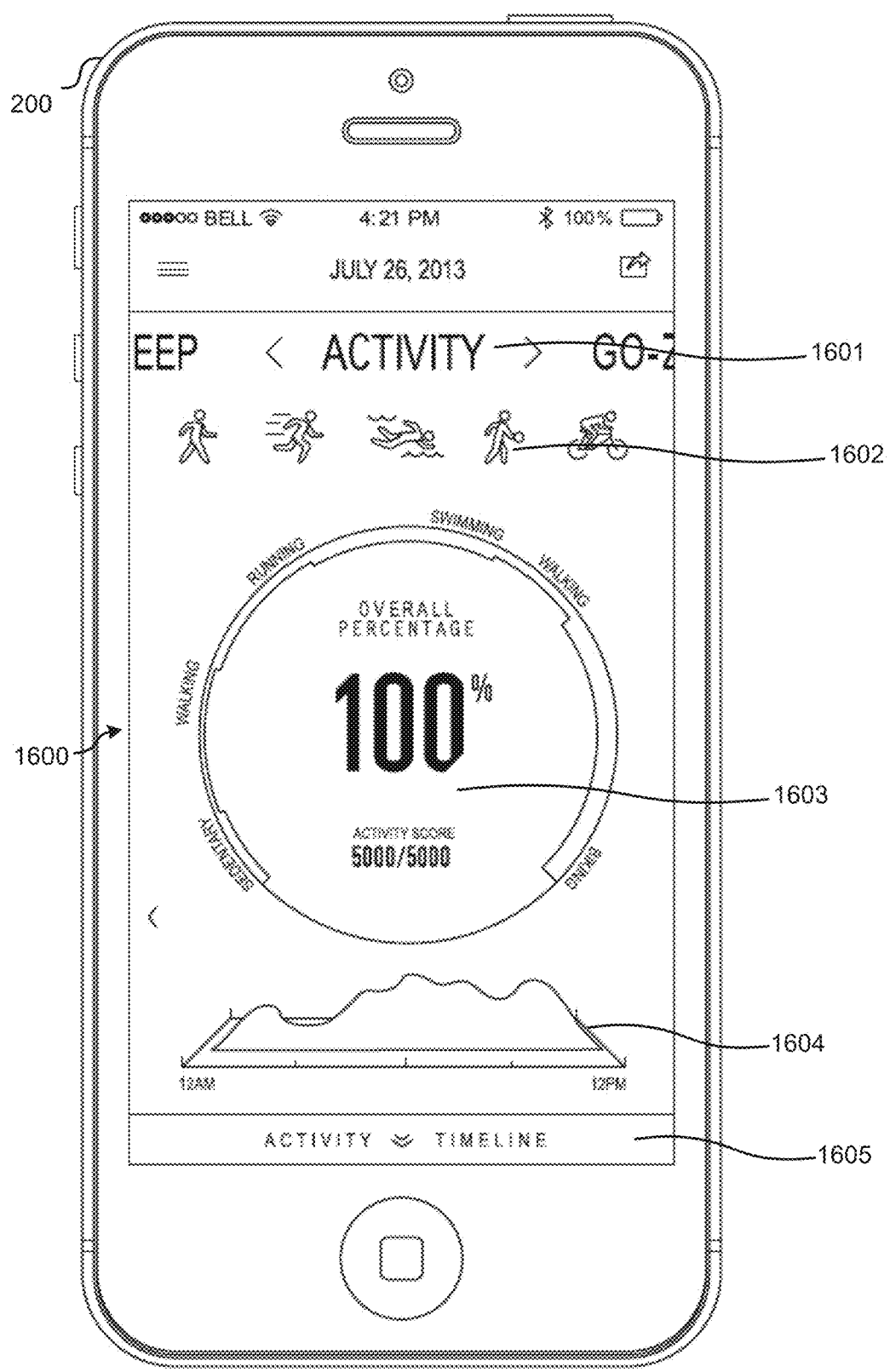
FIG. 14 illustrates an activity display that may be associated with an activity display module of the activity monitoring application of FIG. 4B.

FIG. 14 illustrates an activity display 1600 that may be associated with an activity display module 211. In various embodiments, activity display 1600 may visually present to a user a record of the user's activity. As illustrated, activity display 1600 may comprise a display navigation area 1601, activity icons 1602, activity goal section 1603, live activity chart 1604, and activity timeline 1605. As illustrated in this particular embodiment, display navigation area 1601 allows a user to navigate between the various displays associated with modules 211-214 by selecting "right" and "left" arrows depicted at the top of the display on either side of the display screen title. An identification of the selected display may be displayed at the center of the navigation area 1601. Other selectable displays may displayed on the left and right sides of navigation area 1601. For example, in this embodiment the activity display 1600 includes the identification "ACTIVITY" at the center of the navigation area. If the user wishes to navigate to a sleep display in this embodiment, the user may select the left arrow. In implementations where device 200 includes a touch screen display, navigation between the displays may be accomplished via finger swiping gestures. For example, in one embodiment a user may swipe the screen right or left to navigate to a different display screen. In another embodiment, a user may press the left or right arrows to navigate between the various display screens.

In various embodiments, activity icons 1602 may be displayed on activity display 1600 based on the user's predicted or self-reported activity. For example, in this particular embodiment activity icons 1602 are displayed for the activities of walking, running, swimming, sport, and biking, indicating that the user has performed these five activities. In one particular embodiment, one or more modules of application 210 may estimate the activity being performed (e.g., sleeping, walking, running, or swimming) by comparing the data collected by a biometric earphone's sensors to pre-loaded or learned activity profiles. For example, accelerometer data, gyroscope data, heartrate data, or some combination thereof may be compared to preloaded activity profiles of what the data should look like for a generic user that is running, walking, or swimming. In implementations of this embodiment, the preloaded activity profiles for each particular activity (e.g., sleeping, running, walking, or swimming) may be adjusted over time based on a history of the user's activity, thereby improving the activity predictive capability of the system. In additional implementations, activity display 1600 allows a user to manually select the activity being performed (e.g., via touch gestures), thereby enabling the system to accurately adjust an activity profile associated with the user-selected activity. In this way, the system's activity estimating capabilities will improve over time as the system learns how particular activity profiles match an individual user. Particular methods of implementing this activity estimation and activity profile learning capability are described in U.S. patent application Ser. No. 14/568,835, filed Dec. 12, 2014, titled "System and Method for Creating a Dynamic Activity Profile", and which is incorporated herein by reference in its entirety.

In various embodiments, an activity goal section 1603 may display various activity metrics such as a percentage activity goal providing an overview of the status of an activity goal for a timeframe (e.g., day or week), an activity score or other smart activity score associated with the goal, and activities for the measured timeframe (e.g., day or week). For example, the display may provide a user with a current activity score for the day versus a target activity score for the day. Particular methods of calculating activity scores are described in U.S. patent application Ser. No. 14/137,734, filed Dec. 20, 2013, titled "System and Method for Providing a Smart Activity Score", and which is incorporated herein by reference in its entirety.

In various embodiments, the percentage activity goal may be selected by the user (e.g., by a touch tap) to display to the user an amount of a particular activity (e.g., walking or running) needed to complete the activity goal (e.g., reach 100%). In additional embodiments, activities for the timeframe may be individually selected to display metrics of the selected activity such as points, calories, duration, or some combination thereof. For example, in this particular embodiment activity goal section 1603 displays that 100% of the activity goal for the day has been accomplished. Further, activity goal section 1603 displays that activities of walking, running, biking, and no activity (sedentary) were performed during the day. This is also displayed as a numerical activity score 5000/5000. In this embodiment, a breakdown of metrics for each activity (e.g., activity points, calories, and duration) for the day may be displayed by selecting the activity.

A live activity chart 1604 may also display an activity trend of the aforementioned metrics (or other metrics) as a dynamic graph at the bottom of the display. For example, the graph may be used to show when user has been most active during the day (e.g., burning the most calories or otherwise engaged in an activity).

An activity timeline 1605 may be displayed as a collapsed bar at the bottom of display 1600. In various embodiments, when a user selects activity timeline 1605, it may display a more detailed breakdown of daily activity, including, for example, an activity performed at a particular time with associated metrics, total active time for the measuring period, total inactive time for the measuring period, total calories burned for the measuring period, total distance traversed for the measuring period, and other metrics.

Figure 15:
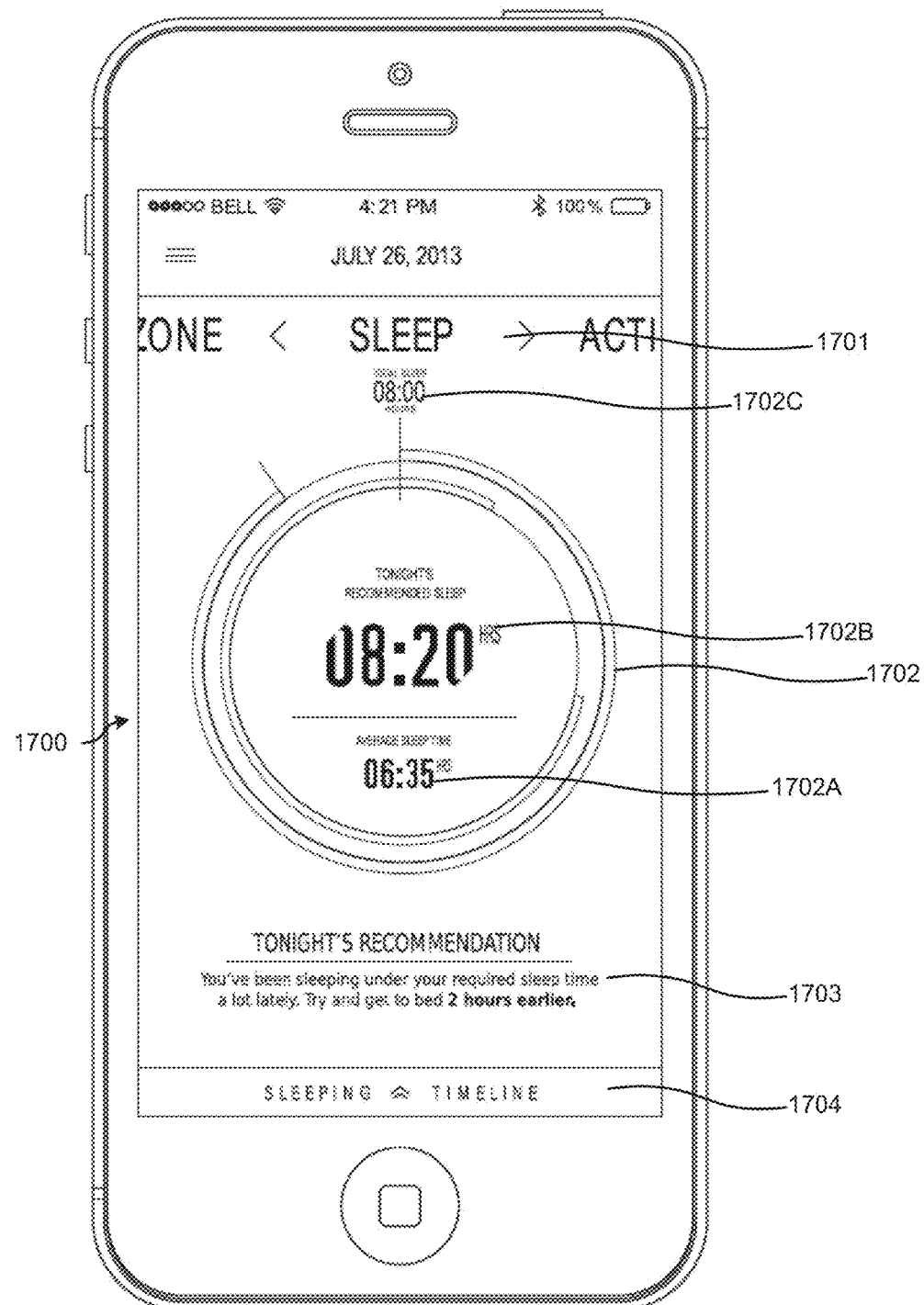
FIG. 15 illustrates a sleep display that may be associated with a sleep display module of the activity monitoring application of FIG. 4B.

FIG. 15 illustrates a sleep display 1700 that may be associated with a sleep display module 1712. In various embodiments, sleep display 1700 may visually present to a user a record of the user's sleep history and sleep recommendations for the day. It is worth noting that in various embodiments one or more modules of the activity tracking application 1710 may automatically determine or estimate when a user is sleeping (and awake) based on an a preloaded or learned activity profile for sleep, in accordance with the activity profiles described above. Alternatively, the user may interact with the sleep display 1700 or other display to indicate that the current activity is sleep, enabling the system to better learn that individualized activity profile associated with sleep. The modules may also use data collected from the earphones, including fatigue level and activity score trends, to calculate a recommended amount of sleep. Systems and methods for implementing this functionality are described in greater detail in U.S. patent application Ser. No. 14/568,835, filed Dec. 12, 2014, and titled "System and Method for Creating a Dynamic Activity Profile", and U.S. patent application Ser. No. 14/137,942, filed Dec. 20, 2013, titled "System and Method for Providing an Interpreted Recovery Score," both of which are incorporated herein by reference in their entirety.

As illustrated, sleep display 1700 may comprise a display navigation area 1701, a center sleep display area 1702, a textual sleep recommendation 1703, and a sleeping detail or timeline 1704. Display navigation area 1701 allows a user to navigate between the various displays associated with modules 211-214 as described above. In this embodiment the sleep display 1700 includes the identification "SLEEP" at the center of the navigation area 1701.

Center sleep display area 1702 may display sleep metrics such as the user's recent average level of sleep or sleep trend 1702A, a recommended amount of sleep for the night 1702B, and an ideal average sleep amount 1702C. In various embodiments, these sleep metrics may be displayed in units of time (e.g., hours and minutes) or other suitable units. Accordingly, a user may compare a recommended sleep level for the user (e.g., metric 1702B) against the user's historical sleep level (e.g., metric 1702A). In one embodiment, the sleep metrics 1702A-1702C may be displayed as a pie chart showing the recommended and historical sleep times in different colors. In another embodiment, sleep metrics 1702A-1702C may be displayed as a curvilinear graph showing the recommended and historical sleep times as different colored, concentric lines. This particular embodiment is illustrated in example sleep display 1700, which illustrates an inner concentric line for recommended sleep metric 1702B and an outer concentric line for average sleep metric 1702A. In this example, the lines are concentric about a numerical display of the sleep metrics.

In various embodiments, a textual sleep recommendation 1703 may be displayed at the bottom or other location of display 1700 based on the user's recent sleep history. A sleeping detail or timeline 1704 may also be displayed as a collapsed bar at the bottom of sleep display 1700. In various embodiments, when a user selects sleeping detail 1704, it may display a more detailed breakdown of daily sleep metrics, including, for example, total time slept, bedtime, and wake time. In particular implementations of these embodiments, the user may edit the calculated bedtime and wake time. In additional embodiments, the selected sleeping detail 1704 may graphically display a timeline of the user's movements during the sleep hours, thereby providing an indication of how restless or restful the user's sleep is during different times, as well as the user's sleep cycles. For the example, the user's movements may be displayed as a histogram plot charting the frequency and/or intensity of movement during different sleep times.

Figure 16:
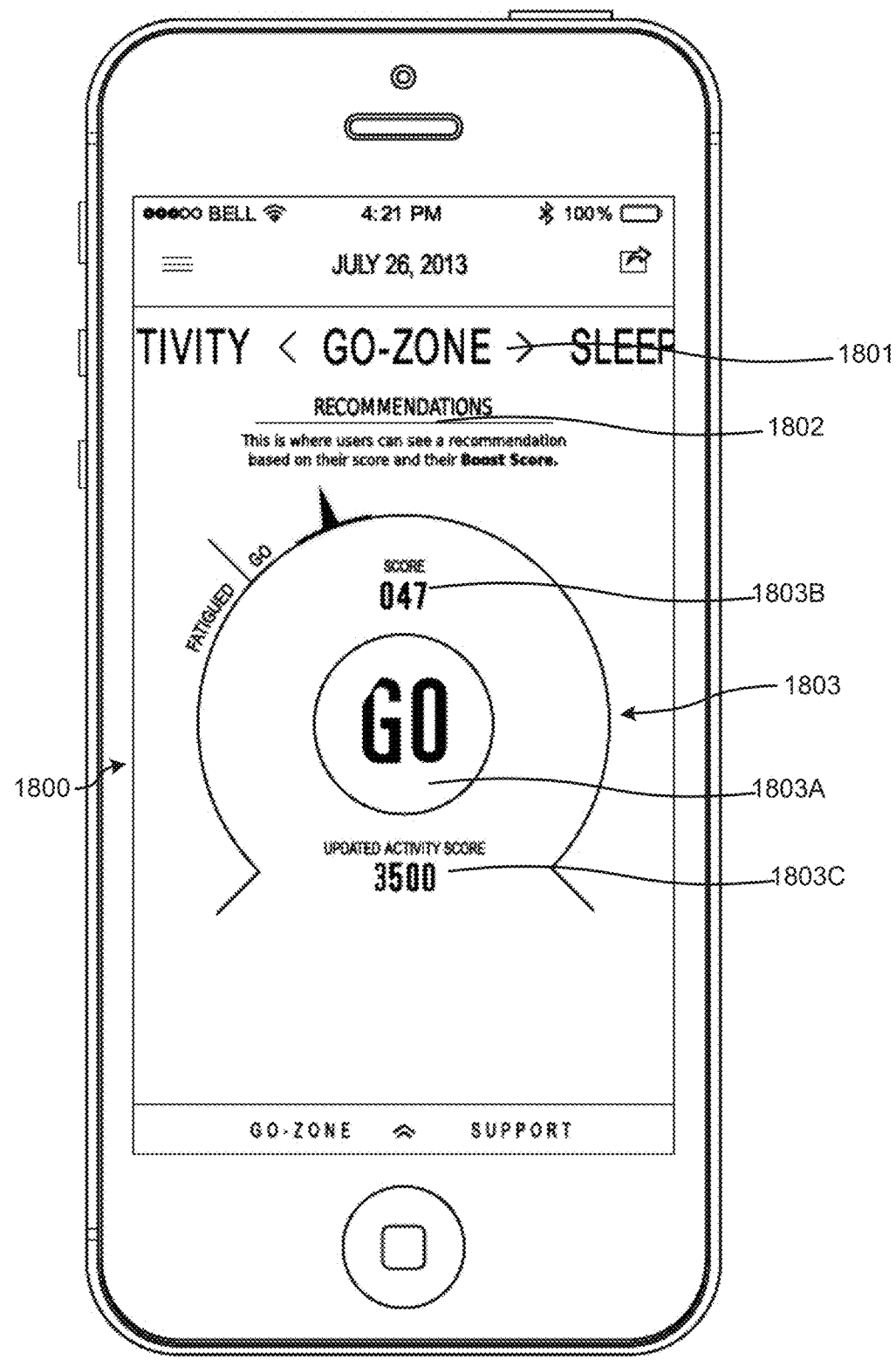
FIG. 16 illustrates an activity recommendation and fatigue level display that may be associated with an activity recommendation and fatigue level display module of the activity monitoring application of FIG. 4B.

FIG. 16 illustrates an activity recommendation and fatigue level display 1800 that may be associated with an activity recommendation and fatigue level display module 213. In various embodiments, display 1800 may visually present to a user the user's current fatigue level and a recommendation of whether or not engage in activity. It is worth noting that one or more modules of activity tracking application 210 may track fatigue level based on data received from the earphones 100, and make an activity level recommendation. For example, HRV data tracked at regular intervals may be compared with other biometric or biological data to determine how fatigued the user is. Additionally, the HRV data may be compared to pre-loaded or learned fatigue level profiles, as well as a user's specified activity goals. Particular systems and methods for implementing this functionality are described above with reference to FIGS. 10-13. Systems and methods for implementing this functionality are also described in greater detail in U.S. patent application Ser. No. 14/140,414, filed Dec. 24, 2013, titled "System and Method for Providing an Intelligent Goal Recommendation for Activity Level", and which is incorporated herein by reference in its entirety.

As illustrated, display 1800 may comprise a display navigation area 1801 (as described above), a textual activity recommendation 1802, and a center fatigue and activity recommendation display 1803. Textual activity recommendation 1002 may, for example, display a recommendation as to whether a user is too fatigued for activity, and thus must rest, or if the user should be active. Center display 1803 may display an indication to a user to be active (or rest) 1803A (e.g., "go"), an overall score 1803B indicating the body's overall readiness for activity, and an activity goal score 1803C indicating an activity goal for the day or other period. In various embodiments, indication 1803A may be displayed as a result of a binary decision—for example, telling the user to be active, or "go"—or on a scaled indicator—for example, a circular dial display showing that a user should be more or less active depending on where a virtual needle is pointing on the dial.

In various embodiments, display 1800 may be generated by measuring the user's HRV at the beginning of the day (e.g., within 30 minutes of waking up.) For example, the user's HRV may be automatically measured using the optical heartrate sensor 122 after the user wears the earphones in a position that generates a good signal as described in method 400. In embodiments, when the user's HRV is being measured, computing device 200 may display any one of the following: an instruction to remain relaxed while the variability in the user's heart signal (i.e., HRV) is being measured, an amount of time remaining until the HRV has been sufficiently measured, and an indication that the user's HRV is detected. After the user's HRV is measured by earphones 100 for a predetermined amount of time (e.g., two minutes), one or more processing modules of computing device 200 may determine the user's fatigue level for the day and a recommended amount of activity for the day. Activity recommendation and fatigue level display 1800 is generated based on this determination.

In further embodiments, the user's HRV may be automatically measured at predetermined intervals throughout the day using optical heartrate sensor 122. In such embodiments, activity recommendation and fatigue level display 1800 may be updated based on the updated HRV received throughout the day. In this manner, the activity recommendations presented to the user may be adjusted throughout the day.

Figure 17:
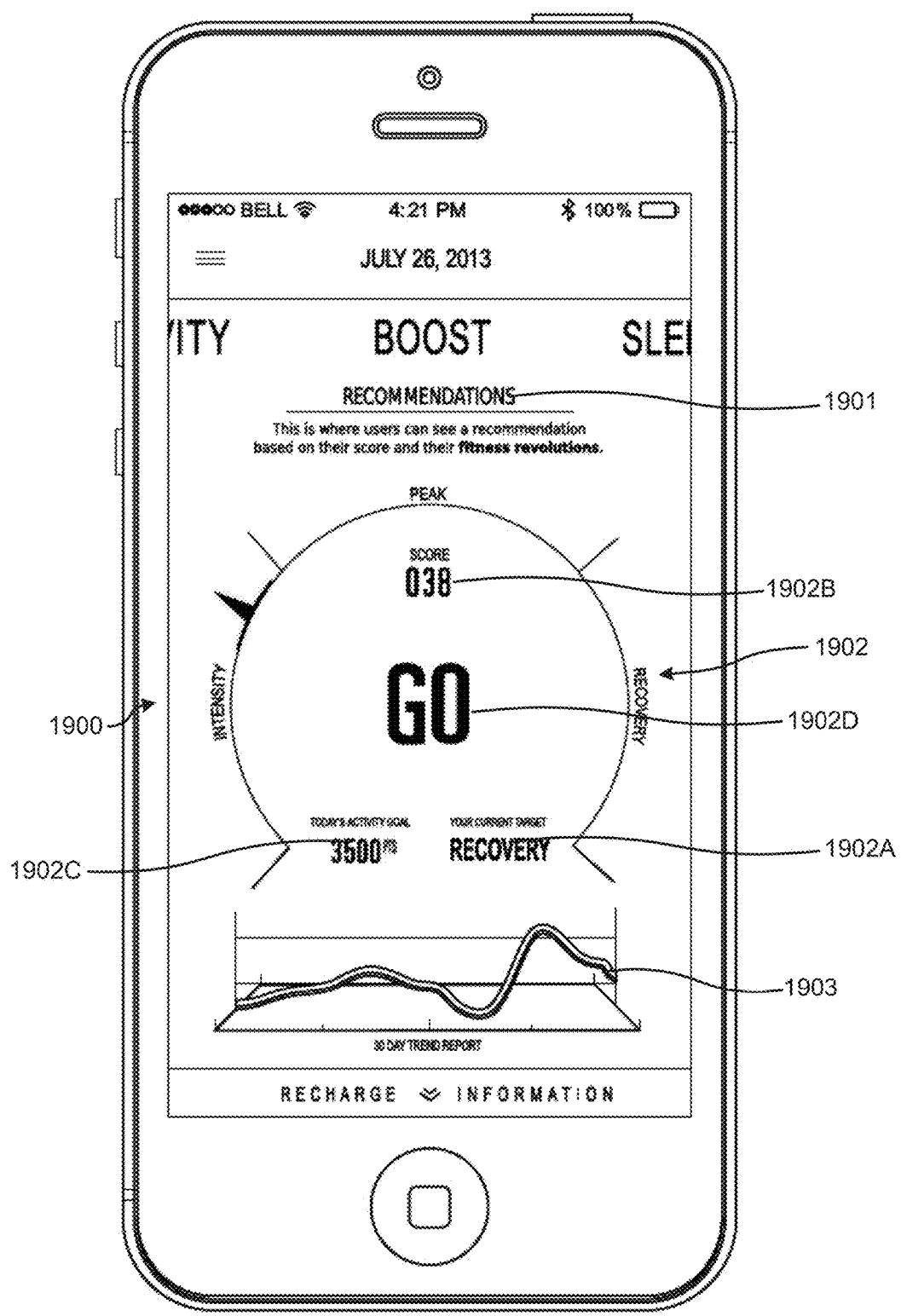
FIG. 17 illustrates a biological data and intensity recommendation display that may be associated with a biological data and intensity recommendation display module of the activity monitoring application of FIG. 4B.

FIG. 17 illustrates a biological data and intensity recommendation display 1900 that may be associated with a biological data and intensity recommendation display module 214. In various embodiments, display 1900 may guide a user of the activity monitoring system through various fitness cycles of high-intensity activity followed by lower-intensity recovery based on the user's body fatigue and recovery level, thereby boosting the user's level of fitness and capacity on each cycle.

As illustrated, display 1900 may include a textual recommendation 1901, a center display 1902, and a historical plot 1903 indicating the user's transition between various fitness cycles. In various embodiments, textual recommendation 1901 may display a current recommended level of activity or training intensity based on current fatigue levels, current activity levels, user goals, pre-loaded profiles, activity scores, smart activity scores, historical trends, and other bio-metrics of interest. Center display 1902 may display a fitness cycle target 1902A (e.g., intensity, peak, fatigue, or recovery), an overall score 1902B indicating the body's overall readiness for activity, an activity goal score 1902C indicating an activity goal for the day or other period, and an indication to a user to be active (or rest) 1902D (e.g., "go"). The data of center display 1902 may be displayed, for example, on a virtual dial, as text, or some combination thereof. In one particular embodiment implementing a dial display, recommended transitions between various fitness cycles (e.g., intensity and recovery) may be indicated by the dial transitioning between predetermined markers.

In various embodiments, display 1900 may display a historical plot 1903 that indicates the user's historical and current transitions between various fitness cycles over a predetermined period of time (e.g., 30 days). The fitness cycles, may include, for example, a fatigue cycle, a performance cycle, and a recovery cycle. Each of these cycles may be associated with a predetermined score range (e.g., overall score 1902B). For example, in one particular implementation a fatigue cycle may be associated with an overall score range of 0 to 33, a performance cycle may be associated with an overall score range of 34 to 66, and a recovery cycle may be associated with an overall score range of 67 to 100. The transitions between the fitness cycles may be demarcated by horizontal lines intersecting the historical plot 1903 at the overall score range boundaries. For example, the illustrated historical plot 1903 includes two horizontal lines intersecting the historical plot. In this example, measurements below the lowest horizontal line indicate a first fitness cycle (e.g., fatigue cycle), measurements between the two horizontal lines indicate a second fitness cycle (e.g., performance cycle), and measurements above the highest horizontal line indicate a third fitness cycle (e.g., recovery cycle).

In various embodiments, the various recommendations and measurements of display 1900 may be generated using the methods described above with reference to FIGS. 10-13.

Figure 18:
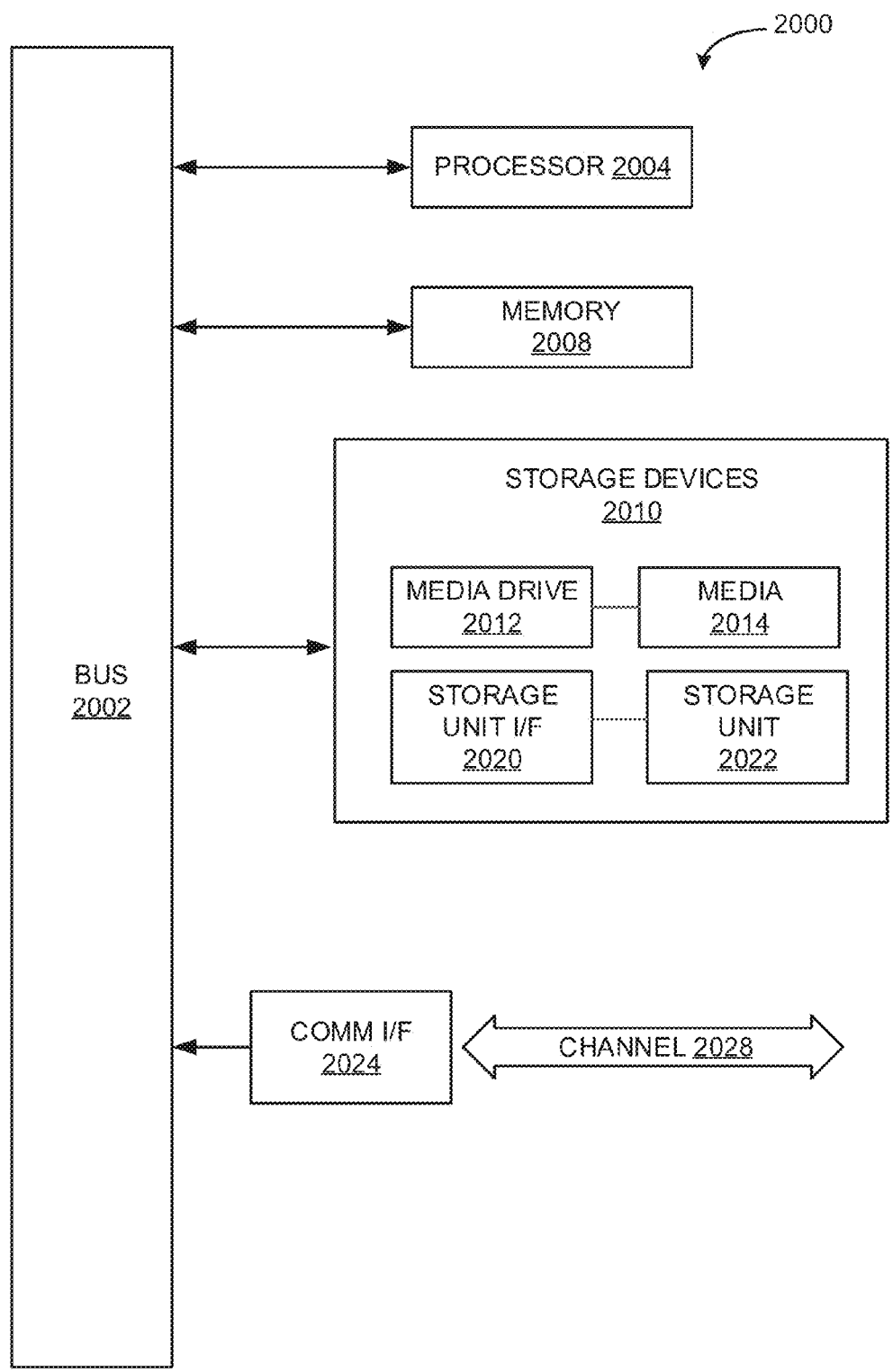
FIG. 18 illustrates an example computing module that may be used to implement various features of the technology disclosed herein.

FIG. 18 illustrates an example computing module that may be used to implement various features of the systems and methods for estimating sky probes disclosed herein. As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 18. Various embodiments are described in terms of this example-computing module 2000. After reading this description, it will become apparent to a person skilled in the relevant art how to implement the application using other computing modules or architectures.

Referring now to FIG. 18, computing module 2000 may represent, for example, computing or processing capabilities found within desktop, laptop, notebook, and tablet computers; hand-held computing devices (tablets, PDA's, smart phones, cell phones, palmtops, etc.); mainframes, supercomputers, workstations or servers; or any other type of special-purpose or general-purpose computing devices as may be desirable or appropriate for a given application or environment. Computing module 2000 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 2000 might include, for example, one or more processors, controllers, control modules, or other processing devices, such as a processor 2004. Processor 2004 might be implemented using a general-purpose or special-purpose processing engine such as, for example, a microprocessor, controller, or other control logic. In the illustrated example, processor 2004 is connected to a bus 2002, although any communication medium can be used to facilitate interaction with other components of computing module 2000 or to communicate externally.

Computing module 2000 might also include one or more memory modules, simply referred to herein as main memory 2008. For example, preferably random access memory (RAM) or other dynamic memory, might be used for storing information and instructions to be executed by processor 2004. Main memory 2008 might also be used for storing temporary variables or other intermediate information during execution of instructions to be executed by processor 2004. Computing module 2000 might likewise include a read only memory ("ROM") or other static storage device coupled to bus 2002 for storing static information and instructions for processor 2004.

The computing module 2000 might also include one or more various forms of information storage mechanism 2010, which might include, for example, a media drive 2012 and a storage unit interface 2020. The media drive 2012 might include a drive or other mechanism to support fixed or removable storage media 2014. For example, a hard disk drive, a solid state drive, a magnetic tape drive, an optical disk drive, a CD, DVD, or Blu-ray drive (R or RW), or other removable or fixed media drive might be provided. Accordingly, storage media 2014 might include, for example, a hard disk, a solid state drive, magnetic tape, cartridge, optical disk, a CD, DVD, Blu-ray or other fixed or removable medium that is read by, written to or accessed by media drive 2012. As these examples illustrate, the storage media 2014 can include a computer usable storage medium having stored therein computer software or data.

In alternative embodiments, information storage mechanism 2010 might include other similar instrumentalities for allowing computer programs or other instructions or data to be loaded into computing module 2000. Such instrumentalities might include, for example, a fixed or removable storage unit 2022 and an interface 2020. Examples of such storage units 2022 and interfaces 2020 can include a program cartridge and cartridge interface, a removable memory (for example, a flash memory or other removable memory module) and memory slot, a PCMCIA slot and card, and other fixed or removable storage units 2022 and interfaces 2020 that allow software and data to be transferred from the storage unit 2022 to computing module 2000.

Computing module 2000 might also include a communications interface 2024. Communications interface 2024 might be used to allow software and data to be transferred between computing module 2000 and external devices. Examples of communications interface 2024 might include a modem or softmodem, a network interface (such as an Ethernet, network interface card, WiMedia, IEEE 802.XX or other interface), a communications port (such as for example, a USB port, IR port, RS232 port BLUETOOTH® interface, or other port), or other communications interface. Software and data transferred via communications interface 2024 might typically be carried on signals, which can be electronic, electromagnetic (which includes optical) or other signals capable of being exchanged by a given communications interface 2024. These signals might be provided to communications interface 2024 via a channel 2028. This channel 2028 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 2008, storage unit 2020, media 2014, and channel 2028. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 2000 to perform features or functions of the present application as discussed herein.

Although described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the application, whether or not such embodiments are described and whether or not such features are presented as being a part of a described embodiment. Thus, the breadth and scope of the present application should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present disclosure should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A system for identifying a performance period, comprising:
   a pair of earphones comprising:
   speakers;
   a processor; and
   a heartrate sensor electrically coupled to the processor, wherein the processor is configured to process electronic input signals from the heartrate sensor; and
   a non-transitory computer-readable medium operatively coupled to at least one of one or more processors and having instructions stored thereon that, when executed by at least one of the one or more processors, cause the system to:
   identify the user's fitness level progression through a plurality of fitness cycles, each fitness cycle of the plurality of fitness cycles comprises a stimulus, a workout activity type, a workout activity period, and a recovery period, wherein identifying the user's fitness level progression through a plurality of fitness cycles is based in part on determining a fatigue level of the user in each fitness cycle based on signals generated by the heartrate sensor;

predict a duration and possible activity types for an optimal future performance period for a future fitness cycle, where the optimal future performance period is calculated based on an interpretive recovery score for each workout activity type detected during the plurality of fitness cycles and a detected current fatigue level, wherein the optimal future performance period begins during the recovery period of a fitness cycle, and wherein the interpretive recovery score is a proportion of a user's fatigue level, wherein the proportion is calculated based on assigned values within a predefined numerical range that are assigned to each of at least one of the user activity type, user activity intensity, duration of user's recent activity and statistical information pertaining to the user's prior activities; and display a recommendation based on the determined predicted optimal future performance period.

2. The system of claim 1, wherein the instructions, when executed by at least one of the one or more processors, further cause the system to determine the current fatigue level occurring in response to the stimulus, wherein the current fatigue level is determined based on signals generated by the heartrate sensor.

3. The system of claim 1, wherein the instructions, when executed by at least one of the one or more processors, further cause the system to determine a recovery level based at least in part, on the fatigue level.

4. The system of claim 1, further comprising a memory, wherein the memory stores an archive comprising learned user characteristics including at least the historical fatigue information of the user.

5. The system of claim 3, wherein the fatigue level and the recovery level are determined based upon the user's heart rate variability and the learned user characteristics, wherein the user's heart rate variability is determined based on the signals generated by the heartrate sensor.

6. The system of claim 1, wherein the recommendation delivered to the user based on the predicted optimal future performance period is displayed textually, numerically or graphically.

7. The system of claim 1, wherein the heartrate sensor is an optical heartrate sensor protruding from a side of the earphone proximal to an interior side of a user's ear when the earphone is worn, and wherein the optical heartrate sensor is configured to measure the user's blood flow and to output an electrical signal representative of this measurement to the earphones processor.

8. The system of claim 1, wherein predicting optimal future performance periods comprises determining periods of time predicted to occur within the recovery period of each of the plurality of fitness cycles during which experiencing additional stimuli promotes future increased fitness levels.

9. The system of claim 1, wherein the pair of earphones further comprise a motion sensor, wherein the earphones processor is configured to process electronic input signals from the motion sensor, and wherein the instructions, when executed by at least one of the one or more processors, further cause the system to monitor a movement of the user based on signals generated by the motion sensor to determine if the movement is indicative of the stimulus.

10. A method of identifying a performance period using earphones with one or more biometric sensors, comprising:

determining heart rate variability data of a user based on signals generated by a heartrate sensor of the earphones;

storing the heart rate variability data in a memory;

identifying a fitness cycle comprising a stimulus, a workout activity type, a workout activity period, and a recovery period determined from fatigue experienced in response to the stimulus, wherein the determined fatigue is based on the heart rate variability data and learned user characteristics stored in a memory; and determining a duration and possible activity type for an optimal future performance period within the fitness cycle calculated based on an interpretive recovery score and a detected current fatigue level, wherein the optimal future performance period begins during the recovery period, and wherein the interpretive recovery score is a proportion of a user's fatigue level, wherein the proportion is calculated based on assigned values within a predefined numerical range that are assigned to each of at least one of the user activity type, user activity intensity, duration of user's recent activity and statistical information pertaining to the user's prior activities; and displaying a recommendation based on the determined predicted optimal future performance period.

11. The method of claim 10, further comprising determining a fatigue level based on the determined fatigue experienced in response to the stimulus, wherein the fatigue level is detected based on the signals generated by the heartrate sensor.

12. The method of claim 11, wherein the determining of the optimal future performance period comprises determining a period during which the fatigue experienced falls within a range of fatigue level values corresponding to a period of recovery within the fitness cycle.

13. The method of claim 12, further comprising determining a recovery level, based at least in part, on the fatigue level.

14. The method of claim 13, further comprising periodically detecting the fatigue level to determine the recovery level.

15. The method of claim 10, wherein the recommendation based on the determined predicted optical future performance period is displayed textually, numerically or graphically.

16. The method of claim 15, wherein the heartrate sensor is an optical heartrate sensor protruding from a side of the earphones proximal to an interior side of a user's ear when the earphone is worn, and wherein the optical heartrate sensor is configured to measure the user's blood flow and to output an electrical signal representative of this measurement.

17. A system for identifying a performance period, comprising:

a pair of earphones comprising:
speakers;
a processor; and
a heartrate sensor electrically coupled to the processor, wherein the processor is configured to process electronic input signals from the heartrate sensor; and
a non-transitory computer-readable medium operatively coupled to at least one of one or more processors and having instructions stored thereon that, when executed by at least one of the one or more processors, cause the system to:

determine a fatigue level associated with fatigue experienced in response to a stimulus, wherein the fatigue level is determined based in part on signals generated by the heartrate sensor;

determine a recovery level based at least in part, on the fatigue level;

identify a fitness cycle, the fitness cycle comprising a stimulus, a workout activity type, a workout activity period, and a recovery period determined from the fatigue experienced in response to the stimulus;

predict a duration and possible activity type for an optimal future performance period based on the identification of the fitness cycle, a detected current fatigue level, wherein the optimal future performance period begins during the recovery period, and wherein the interpretive recovery score is calculated by determining a proportion of a user's fatigue level, wherein the proportion is calculated based on assigned values within a predefined numerical range that are assigned to each of at least one of the user activity type, user activity intensity, duration of user's recent activity and statistical information pertaining to the user's prior activities; and display a recommendation based on the determined predicted optimal future performance period.

18. The system of claim 17, wherein the pair of earphones further comprise a motion sensor, wherein the earphones processor is configured to process electronic input signals from the motion sensor, and wherein the instructions, when executed by at least one of the one or more processors, further cause the system to monitor a movement of the user based on signals generated by the motion sensor to determine if the movement is indicative of the stimulus.

19. The system of claim 18, wherein the fatigue level and the recovery level are determined based upon the user's heart rate variability and learned user characteristics, wherein the user's heart rate variability is determined based on the signals generated by the heartrate sensor.

20. The system of claim 18, wherein the recommendation based on the optimal future performance period and data characterizing the identified fitness cycle is presented to a user via an electronic display.

* * * * *